US008062869B2

(12) United States Patent
Nakanishi et al.

(10) Patent No.: US 8,062,869 B2
(45) Date of Patent: *Nov. 22, 2011

(54) METHOD FOR PRODUCING L-LYSINE

(75) Inventors: Kazuo Nakanishi, Kawasaki (JP);
Yoshimi Kikuchi, Kawasaki (JP);
Junichiro Kojima, Kawasaki (JP);
Tomoko Suzuki, Kawasaki (JP);
Yasushi Nishimura, Kawasaki (JP);
Hiroyuki Kojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/721,813

(22) Filed: Mar. 11, 2010

(65) Prior Publication Data
US 2010/0173368 A1 Jul. 8, 2010

Related U.S. Application Data

(63) Continuation of application No. 10/149,450, filed as application No. PCT/JP00/00298 on Jan. 21, 2000, now Pat. No. 7,723,081.

(51) Int. Cl.
*C12P 13/08* (2006.01)
(52) U.S. Cl. .......... 435/115; 435/252; 435/325; 435/7.1
(58) Field of Classification Search .................... None
See application file for complete search history.

(56) References Cited

U.S. PATENT DOCUMENTS

| | | | |
|---|---|---|---|
| 4,346,170 A | 8/1982 | Sano et al. | |
| 5,827,698 A | 10/1998 | Kikuchi et al. | |
| 5,830,716 A | 11/1998 | Kojima et al. | |
| 5,876,983 A | 3/1999 | Sugimoto et al. | |
| 5,919,694 A | 7/1999 | Sugimoto et al. | |
| 5,932,453 A | 8/1999 | Kikuchi et al. | |
| 6,040,160 A | 3/2000 | Kojima et al. | |
| 6,200,785 B1 | 3/2001 | Kreutzer et al. | |
| 7,090,998 B2 | 8/2006 | Ishikawa et al. | |
| 7,097,999 B2 | 8/2006 | Tsujimoto et al. | |
| 7,252,972 B2 | 8/2007 | Kikuchi et al. | |
| 7,306,933 B2 | 12/2007 | Van Dien et al. | |
| 7,399,617 B1 | 7/2008 | Livshits et al. | |
| 7,524,656 B2 | 4/2009 | Livshits et al. | |
| 7,527,950 B2 | 5/2009 | Livshits et al. | |
| 2002/0110876 A1 | 8/2002 | Miyata et al. | |
| 2002/0160461 A1 | 10/2002 | Nakai et al. | |
| 2003/0049804 A1 | 3/2003 | Pompejus et al. | |
| 2004/0126854 A1 | 7/2004 | Hanke et al. | |
| 2004/0265956 A1 | 12/2004 | Takikawa et al. | |
| 2006/0019367 A1 | 1/2006 | Umezawa et al. | |
| 2006/0205043 A1 | 9/2006 | Tsujimoto et al. | |
| 2007/0184525 A1 | 8/2007 | Date et al. | |
| 2007/0254345 A1 | 11/2007 | Fukui et al. | |
| 2009/0148915 A1 | 6/2009 | Van Dien et al. | |

FOREIGN PATENT DOCUMENTS

| | | |
|---|---|---|
| DE | 38 23 451 | 1/1990 |
| EP | 0 318 663 | 6/1989 |
| EP | 0 723 011 | 7/1996 |
| EP | 0 733 710 | 9/1996 |
| EP | 0 733 712 | 9/1996 |
| WO | 95/16042 | 6/1995 |

OTHER PUBLICATIONS

Chatterjee, M., et al., "Microbial Production of L-lysine: A Review," Hind. Antibiot. Bull. 1997, vol. 39, pp. 20-49.
Jetten, M. S. M., et al., "Recent Advances in the Physiology and Genetics of Amino Acid-Producing Bacteria," Critical Rev. Biotechnol. 1995;15(1):73-103.
Vauterni, M., et al., "Functional rescue of a bacterial dapA auxotroph with a plant cDNA library selects for mutant clones encoding a feedback-insensitive dihydrodipicolinate synthase," The Plant Journal 2000;21(3):239-248.
English translation of Third Party Letter (Degussa) to European Patent Office concerning the patentability of the invention, dated Jul. 26, 2007, pp. 1-7.
Office Communication from EP Patent App. No. 00900872.3 (Sep. 17, 2007).
Supplementary European Search Report for EP Patent App. No. 00900872.3 (Jun. 23, 2004).

*Primary Examiner* — Hope Robinson
(74) *Attorney, Agent, or Firm* — Shelly Guest Cermak; Cermak Nakajima LLP

(57) ABSTRACT

An *Escherichia* bacterium having dihydrodipicolinate synthase and aspartokinase, both of which are desensitized to feedback inhibition by L-lysine. The intracellular activity of dihydrodipicolinate reductase in this bacterium can also be enhanced. Furthermore, a diaminopimelate dehydrogenase gene can be introduced into this bacterium, or intracellular activities of tetrahydrodipicolinate succinylase and succinyl diaminopimelate deacylase can be enhanced. Finally, the intracellular activities of aspartate-semialdehyde dehydrogenase or phosphoenolpyruvate carboxylase can be enhanced in this bacterium. The bacterium can be cultured in a suitable medium to produce and accumulate L-lysine in culture, and the L-lysine is collected from the culture.

4 Claims, 20 Drawing Sheets

METHOD FOR PRODUCING L-LYSINE

This application is a continuation under 35 U.S.C. §120 of U.S. patent application Ser. No. 10/149,450, filed on Jun. 27, 2002 now U.S. Pat. No. 7,723,081, which was a national phase filing under 35 U.S.C. §371 of PCT Patent Application No. PCT/JP00/00298, filed Jan. 21, 2000, which are incorporated in their entireties by reference. The Sequence Listing in electronic format filed herewith is also hereby incorporated by reference in its entirety (File Name: 2010-03-11T_US-134C_Seq_List; File Size: 2 KB; Date Created: Mar. 11, 2010).

BACKGROUND OF THE INVENTION

1. Field of the Invention

The present invention relates to the microbial industry. More specifically, the present invention relates to a method for producing L-lysine by fermentation, and a microorganism used in the production method.

2. Brief Description of the Related Art

In the production of L-lysine by fermentation, strains isolated from nature or artificial mutants thereof have conventionally been used to improve the productivity. Many artificial mutant strains that produce L-lysine are known, and include S-2-aminoethylcysteine (AEC) resistant strains and those that belong to the genus *Brevibacterium, Corynebacterium, Bacillus* or *Escherichia*. Furthermore, various techniques have been disclosed for increasing the amino acid production, for example, the use of a transformant obtained by using recombinant DNA.

As for *Escherichia* bacteria, for example, methods for producing L-lysine by using a strain in which dihydrodipicolinate synthase (DDPS) activity is enhanced have been disclosed in Japanese Patent Application Laid-open (Kokai) No. 56-18596, U.S. Pat. No. 4,346,170 and Applied Microbiology and Biotechnology, 15, pp. 227-331 (1982). Furthermore, a method for producing L-lysine by using an *Escherichia* bacterium into which DDPS derived from, and native to, a *Corynebacterium* bacterium has been introduced is disclosed in Korean Patent Publication No. 92-8382. Furthermore, a method for producing L-lysine using a strain which has been transformed with a plasmid containing DNA that codes for dihydrodipicolinate synthase derived from, and native to, an *Escherichia* bacterium which has a mutation to desensitize feedback inhibition by L-lysine, DNA that codes for aspartokinase which is desensitized to feedback inhibition by L-lysine, DNA that codes for dihydrodipicolinate reductase, and DNA that codes for diaminopimelate dehydrogenase derived from, and native to, a coryneform bacterium is disclosed in International Publication No. WO95/16042.

As for *Brevibacterium* bacteria, International Publication No. WO95/11985 discloses that L-lysine productivity can be improved by enhancing the activity of intracellular nicotinamide adenine dinucleotide transhydrogenase. Furthermore, a method for producing L-lysine using a strain in which phosphoenolpyruvate carboxylase activity is solely enhanced and a method for producing L-lysine using a strain in which aspartate-semialdehyde dehydrogenase activity is solely enhanced are disclosed in Japanese Patent Application Laid-open No. 60-87788 and Japanese Patent Publication (Kokoku) No. 6-102028, respectively.

The industrial production of amino acids by fermentation is performed on a large scale. Therefore, even improving the yield by several percent may provide significant industrial value, and thus improving the yield, even if only a small amount, is desirable.

SUMMARY OF THE INVENTION

It is an aspect of the present invention is to provide an improved method for producing L-lysine by fermentation compared with the conventional methods.

The present inventors assiduously studied in order to achieve the aforementioned object. As a result, they found that, if the activity of aspartate-semialdehyde dehydrogenase or phosphoenolpyruvate carboxylase was enhanced in an *Escherichia* bacterium having a specified property, and if activity or activities of a specific enzyme or enzymes were enhanced in addition to the aforementioned enzymes in such an *Escherichia* bacterium, the productivity of the bacterium for L-lysine could be improved.

That is, the present invention provides:

in a first aspect, an *Escherichia* bacterium in which (1) intracellular activities of dihydrodipicolinate synthase, aspartokinase and dihydrodipicolinate reductase are enhanced, and (2) intracellular activity of diaminopimelate dehydrogenase or intracellular activities of tetrahydrodipicolinate succinylase and succinyl diaminopimelate deacylase is/are enhanced, wherein intracellular activity of aspartate-semialdehyde dehydrogenase or phosphoenolpyruvate carboxylase is enhanced;

in a second aspect, an *Escherichia* bacterium in which (1) intracellular activities of dihydrodipicolinate synthase, aspartokinase and dihydrodipicolinate reductase are enhanced, and (2) intracellular activity of diaminopimelate dehydrogenase or intracellular activities of tetrahydrodipicolinate succinylase and succinyl diaminopimelate deacylase is/are enhanced, wherein intracellular activity of phosphoenolpyruvate carboxylase and intracellular activity of nicotinamide adenine dinucleotide transhydrogenase or aspartate-semialdehyde dehydrogenase are enhanced; and in a third aspect, an *Escherichia* bacterium in which (1) intracellular activities of dihydrodipicolinate synthase, aspartokinase and dihydrodipicolinate reductase are enhanced, and (2) intracellular activity of diaminopimelate dehydrogenase or intracellular activities of tetrahydrodipicolinate succinylase and succinyl diaminopimelate deacylase is/are enhanced, wherein intracellular activities of phosphoenolpyruvate carboxylase and nicotinamide adenine dinucleotide transhydrogenase and intracellular activity of aspartate-semialdehyde dehydrogenase or aspartase are enhanced (hereinafter, the bacteria according to the aforementioned three aspects are also collectively referred to as the "bacteria of the present invention").

The intracellular activities of aspartate-semialdehyde dehydrogenase and aspartase are enhanced in the bacteria.

Furthermore, aspartokinase, dihydrodipicolinate reductase, tetrahydrodipicolinate succinylase, succinyl diaminopimelate deacylase, phosphoenolpyruvate carboxylase and aspartate-semialdehyde dehydrogenase are each derived from an *Escherichia* bacterium, nicotinamide adenine dinucleotide transhydrogenase and aspartase, if present, are each derived from an *Escherichia* bacterium, dihydrodipicolinate synthase is derived from an *Escherichia* bacterium or a *Brevibacterium* bacterium, and diaminopimelate dehydrogenase is derived from a *Brevibacterium* bacterium.

The intracellular activity of an enzyme can be enhanced by any of the following methods, or any combination thereof.

(1) Introduction of a plasmid having a gene encoding the enzyme.

(2) Increase of copy number of a gene encoding the enzyme on the chromosome.

(3) Modification of a promoter sequence of a gene encoding the enzyme on the chromosome.

Furthermore, the intracellular activities of dihydrodipicolinate synthase and aspartokinase are enhanced by harboring dihydrodipicolinate synthase and aspartokinase, both of which are desensitized to feedback inhibition by L-lysine, and the intracellular activity of diaminopimelate dehydrogenase is enhanced by introduction of a diaminopimelate dehydrogenase gene.

It is a further aspect of the present invention to provide a method for producing L-lysine, which comprises culturing any of the bacteria as described herein in a suitable medium to produce and accumulate L-lysine in the culture, and collecting the L-lysine from the culture.

DESCRIPTION OF THE PREFERRED EMBODIMENTS

<1> Bacteria of the Present Invention

Figure 1:
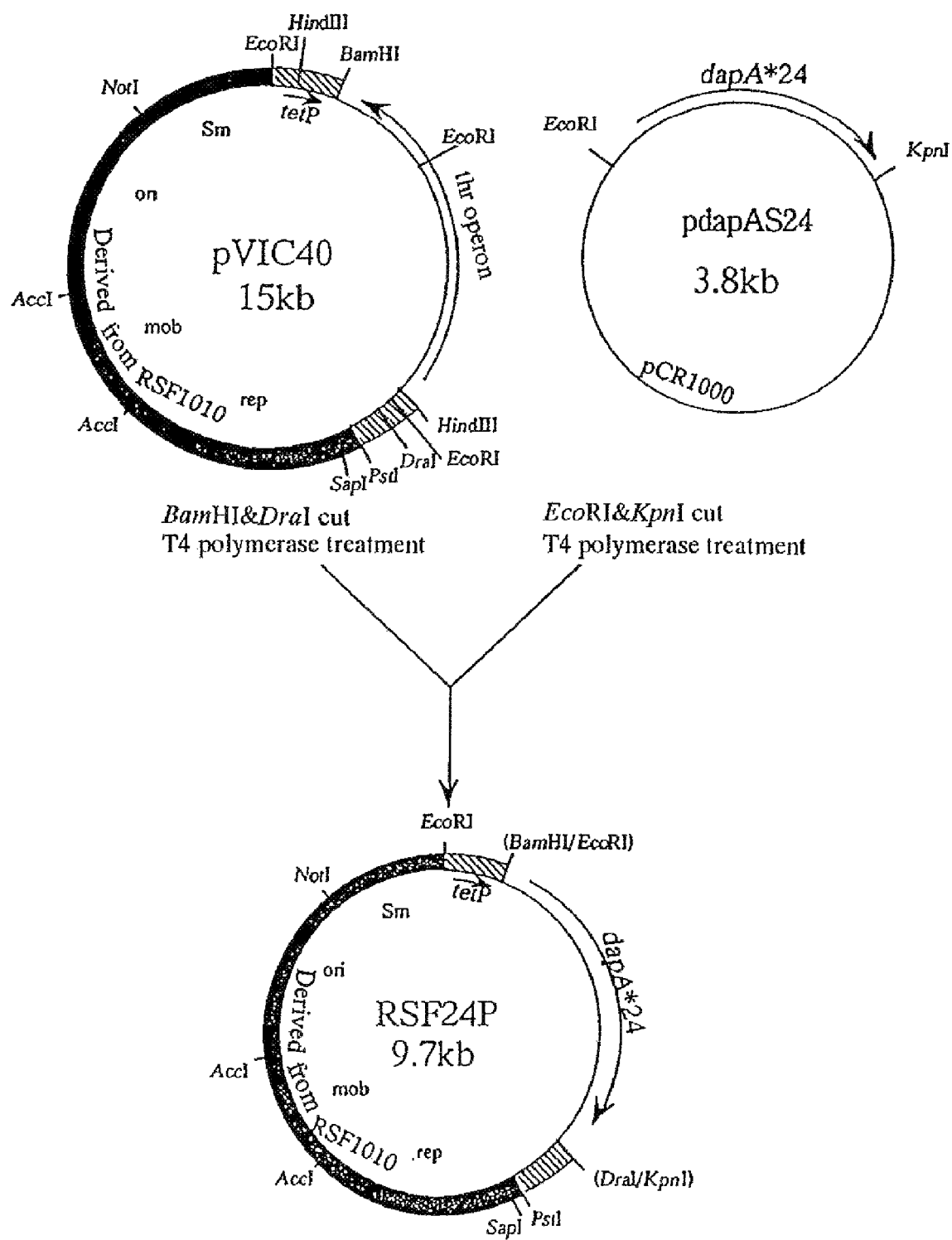
FIG. 1 shows a process of producing the plasmid RSF24P from RSF1010, which contains dapA*24.

The bacteria of the present invention include *Escherichia* bacteria in which (1) intracellular activities of dihydrodipicolinate synthase, aspartokinase and dihydrodipicolinate reductase are enhanced, (2) intracellular activity of diaminopimelate dehydrogenase, or intracellular activities of tetrahydrodipicolinate succinylase and succinyl diaminopimelate deacylase is/are enhanced, and (3) the intracellular activities of the following enzymes are further enhanced:

(a) aspartate-semialdehyde dehydrogenase or phosphoenolpyruvate carboxylase, (b) phosphoenolpyruvate carboxylase, and nicotinamide adenine dinucleotide transhydrogenase (hereinafter also referred to as "transhydrogenase") or aspartate-semialdehyde dehydrogenase, or (c) phosphoenolpyruvate carboxylase and transhydrogenase, and aspartate-semialdehyde dehydrogenase or aspartase.

The bacteria of the present invention can include *Escherichia* bacteria in which intracellular activities of phosphoenolpyruvate carboxylase, transhydrogenase, aspartate-semialdehyde dehydrogenase and aspartase are further enhanced.

The bacteria of the present invention can include strains of *Escherichia coli* (*E. coli*).

The expression "intracellular activity is enhanced" can mean that the intracellular enzymatic activity is increased as compared with a wild-type strain (for example, an *E. coli* W3110 strain), or a parent strain (a strain with no enhanced intracellular activities), and also can mean that a bacterium has an enzymatic activity not typically present in the wild-type or parent strain. The methods for measuring the activities of the aforementioned enzymes are known, and the increase in their intracellular activities can be easily confirmed by those skilled in the art.

Methods for enhancing the intracellular activities include the following, but are not limited to these.

Specifically, the following are methods for increasing the expression of enzymes.

(1) Introduction of Plasmid Containing Gene of Enzyme

As the plasmid, a vector that is autonomously replicable in an *Escherichia* bacterium cell can be used. It can be introduced by a known method. That is, the gene of interest can be inserted into the vector, and the vector can be used to transform an *Escherichia* bacterium. This vector can be a multicopy type plasmid.

The genes can be on the same plasmid or on different plasmids. Some of the genes can be on the same plasmid. When two or more kinds of plasmids are used, plasmids can be used that have stable partitioning systems so that they are able to stably co-exist in a cell. The order in which the genes are introduced is not particularly limited.

(2) Increasing the Copy Number of the Gene Encoding the Enzyme on the Cellular Chromosome The copy number can be increased by amplifying the DNA on the chromosomal DNA using Mu phage or the like.

DNA on the chromosomal DNA can be that which is native to *Escherichia* bacteria, or DNA which is incorporated into the chromosome of the host microorganism by a method using transduction, transposon (Berg, D. E. and Berg C. M., Bio/Technol., 1, 417 (1983)), Mu phage (Japanese Patent Application Laid-open No. 2-109985), or homologous recombination (Experiments in Molecular Genetics and Cold Spring Harbor Lab. (1972)).

(3) Modification of the Promoter Sequence of the Gene Encoding the Enzyme

A promoter sequence can be modified to increase transcription of a gene and thereby increase the amount which is expressed. For example, the promoter can be enhanced by introducing a mutation into the promoter to increase the transcription amount of a gene that is located downstream from the promoter. Other methods include introducing a promoter that is able to function in *Escherichia* bacteria, such as lac, trp, tac, trc, and PL. Alternatively, gene transcription can be increased by introducing an enhancer. The promoter can be on the chromosome or a plasmid. Introducing genes and/or promoters into chromosomal DNA is described in Japanese Patent Application Laid-open No. 1-215280, for example.

The origins of the genes which enocode the aforementioned enzymes are not particularly limited, and genes obtained from various origins can be used so long as the genes can be expressed and the genetic products can function in *Escherichia* bacteria.

Hereinafter, methods which can be used to obtain the L-lysine biosynthesis system genes and transhydrogenase gene of *E. coli*, as well as the dihydrodipicolinate synthase and diaminopimelate dehydrogenase genes of *Brevibacterium lactofermentum* are exemplified.

A phosphoenolpyruvate carboxylase gene (ppc) can be obtained from the plasmid pS2 (Sabe, H. et al., Gene, 31, 279 (1984)) or pT2, both of which contain this gene. A DNA fragment that contains ppc can be obtained by digesting pS2 with AatII and AflIII. Furthermore, a DNA fragment that contains ppc can also be obtained by digesting pT2 with SmaI and ScaI. An *E. coli* F15 strain harboring pT2 (AJ12873) was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Jul. 15, 1993, and received an accession number of FERM P-13752. Then, it was converted to an international deposit under the provisions of the Budapest Treaty on Jul. 11, 1994, and received an accession number of FERM BP-4732.

An aspartokinase gene (lysC) can be obtained by amplification by PCR using the *E. coli* chromosomal DNA as a template and two kinds of oligonucleotide primers prepared based on the known nucleotide sequence of lysC (Cassan, M., Parsot, C., Cohen, G. N., and Patte, J. C., J. Biol. Chem., 261, 1052 (1986) (for example, see SEQ ID NOS: 5 and 6 in International Publication No. WO95/16042).

An aspartate-semialdehyde dehydrogenase gene (asd) can be obtained from the plasmid pAD20 (Haziza, C. et al., EMBO, 1, 379 (1982)), which contains this gene. If pAD20 is digested with AseI and ClaI, a DNA fragment containing asd will be obtained.

A dihydrodipicolinate synthase gene (dapA) can be obtained by amplification by PCR using the *E. coli* chromosomal DNA as a template and two kinds of oligonucleotide primers (for example, SEQ ID NOS: 1 and 2 reported by International Publication No. WO95/16042) prepared based on the known nucleotide sequence of dapA (Richaud, F. et al., J. Bacteriol., 297 (1986)).

A dihydrodipicolinate reductase gene (dapB) can be obtained by amplification by PCR using the *E. coli* chromosomal DNA as a template and two kinds of oligonucleotide primers (for example, SEQ ID NOS: 9 and 10 reported in International Publication No. WO95/16042) prepared based on the known nucleotide sequence of dapB (Bouvier, J. et al., J. Biol. Chem., 259, 14829 (1984)).

A tetrahydrodipicolinate succinylase gene (dapD) can be obtained by amplification by PCR using the *E. coli* chromosomal DNA as a template and two kinds of oligonucleotide primers (for example, SEQ ID NOS: 15 and 16 reported in International Publication No. WO95/16042) prepared based on the known nucleotide sequence of dapD (Richaud, C. et al., J. Biol. Chem., 259, 14824 (1984)).

A succinyl diaminopimelate deacylase gene (dapE) can be obtained by amplification by PCR using the *E. coli* chromosomal DNA as a template and two kinds of oligonucleotide primers (for example, SEQ ID NOS: 17 and 18 reported in International Publication No. WO95/16042) prepared based on the known nucleotide sequence of dapE (Bouvier, J. et al., J. Bacteriol., 174, 5265 (1992)).

An aspartase gene (aspA) can be obtained by amplification by PCR using the *E. coli* chromosomal DNA as a template and two kinds of oligonucleotide primers (for example, SEQ ID NOS: 5 and 6 reported in the Sequence Listing of the present specification) prepared based on the known nucleotide sequence of aspA (Woods, S. A. et al., Biochem. J., 237 (2), 547-557 (1986)).

A transhydrogenase gene (pntAB) can be prepared based on the known nucleotide sequence of the transhydrogenase gene (D. M. Clarke et al., Eur. J. Biochem., 158, 647-653 (1986)). In *E. coli*, transhydrogenase is composed of two subunits, which are encoded by pntA and pntB (D. M. Clarke et al., supra). Therefore, Both gene subunits can be prepared (see, for example, International Publication No. WO95/11985).

The genes can also be obtained from a plasmid containing pntAB, such as pMW::THY (International Publication No. WO95/11985). This plasmid is obtained by ligating a 3.0 kb DNA fragment from the *E. coli* K-12 MC1061 strain, which contains pntA and pntB, as well as a BamHI and HindIII fragment from the plasmid vector pMW118. An *Escherichia coli* JM109 strain harboring pMW::THY was designated as AJ12929, and deposited at the National Institute of Bioscience and Human-Technology, Agency of Industrial Science and Technology, Ministry of International Trade and Industry (postal code 305-0046, 1-3 Higashi 1-chome, Tsukuba-shi, Ibaraki-ken, Japan) on Oct. 4, 1993, and received an accession number of FERM P-13890. Then, it was converted to an international deposit under the provisions of the Budapest Treaty on Sep. 11, 1994, and received an accession number of FERM BP-4798.

The dihydrodipicolinate synthase gene (dapA) from *Brevibacterium lactofermentum* can be obtained by amplification by PCR using the chromosomal DNA of *Brevibacterium lactofermentum* as a template and two kinds of oligonucleotide primers (for example SEQ ID NOS: 3 and 4 reported in the Sequence Listing of the present specification) prepared based on the known nucleotide sequence of dapA (Bonassie, S. et al., N.A.R., 18 (21), 6421 (1990)).

The diaminopimelate dehydrogenase gene (ddh) from *Brevibacterium lactofermentum* can be obtained by amplification by PCR using the chromosomal DNA of *Brevibacterium lactofermentum* as a template and two kinds of oligonucleotide primers (for example, SEQ ID NOS: 11 and 12 reported in International Publication No. WO95/16042) prepared based on the known nucleotide sequence of ddh from *Corynebacterium glutamicum* (Ishino, S. et al., Nucleic Acids Res., 15, 3917 (1987)).

To enhance intracellular activities of the enzymes, the specific activities of the enzymes can also be increased. This method may be combined with the methods described herein for increasing the expression of the genes encoding the enzymes.

To increase the specific activities of the enzymes, a mutation can be made in the enzyme to desensitize the feedback inhibition by the produced metabolite, and so forth.

Examples of enzymes in which feedback inhibition has been desensitized include dihydrodipicolinate synthase (DDPS) and aspartokinase (AK), both of which have been desensitized to L-lysine.

The phrase "feedback inhibition by L-lysine is desensitized" means that substantial desensitization of the inhibition is sufficient, and it is not required that the inhibition is completely desensitized. Furthermore, desensitized enzymes derived from organisms other than *Escherichia* bacteria can also be used, irrespective of whether it is a wild-type or mutant type enzyme, if the degree of the feedback inhibition by L-lysine is lower than that of a wild-type enzyme derived from an *Escherichia* bacterium. Therefore, an enzyme that, in it's native form, is not subject to feedback inhibition by L-lysine, such as DDPS derived from *Brevibacterium* bacteria, is also included.

The degree of the feedback inhibition by L-lysine can be evaluated by known methods such as those described in International Publication No. WO95/16042, Examples 1 and 2.

DDPS and AK which have been desensitized to feedback inhibition by L-lysine are disclosed in International Publication No. WO95/16042 and Japanese Patent Application Laid-open No. 10-113183.

That is, examples of desensitized DDPS include DDPS enzymes that have been mutated to obtain the desensitization to the feedback inhibition by L-lysine. The DDPS from *Escherichia* bacteria, and *E. coli*, are exemplary. Examples of the mutation that desensitizes the feedback inhibition by L-lysine in DDPS include:

(1) replacing the alanine residue at position 81 with another amino acid residue (valine, for example), (2 replacing the histidine residue at position 118 with another amino acid residue (tyrosine, for example), and (3) replacing the alanine residue at position 81 with another amino acid residue (valine, for example), and replacing the histidine residue at position 118 with another amino acid residue (tyrosine, for example) in the DDPS of *E. coli* (see SEQ ID NO: 4 in International Publication No. WO95/16042), as counted from N-terminus. It is well known that differences may occur among amino acid sequences from different species or strains, although these differences may not affect activity, and an amino acid residue corresponding to the aforementioned specific amino acid residues can be easily recognized by those skilled in the art.

Other examples of a desensitized DDPS include DDPS derived from coryneform bacteria, for example, *Brevibacterium lactofermentum* (Cremer J. et al., J. Gen. Microbiol., 134, 3221-3229 (1988)).

In order to obtain an *Escherichia* bacteria which contains a desensitized DDPS, for example, DNA that encodes the desensitized DDPS can be introduced.

Examples of the DNA coding for desensitized DDPS include DNA coding for a wild-type DDPS which includes a mutation which results in a DDPS which is desensitized to feedback inhibition by L-lysine.

Hereinafter, a method for obtaining DNA coding for desensitized DDPS (desensitized DDPS gene) will be explained by exemplifying DDPS derived from *Escherichia* bacteria, although DNA encoding DDPS from other organisms can be similarly obtained. Furthermore, if a wild-type DDPS derived from another organism is a desensitized DDPS, DNA coding for it can be used as it is.

The DNA coding for wild-type DDPS is not particularly limited so long as it codes for DDPS derived from an *Escherichia* bacterium. Specifically, DNA coding for the amino acid sequence shown in International Publication No. WO95/16042, SEQ ID NO: 4, can be used. More specifically, the sequence of nucleotide numbers 272-1147 within the nucleotide sequence shown in SEQ ID NO: 3 of International Publication No. WO95/16042 can be used. In these sequences, mutations of the nucleotide sequence such as those recited above will result in a DNA coding for a desensitized DDPS. Furthermore, slight differences in the amino acid sequences of DDPS among bacterial species and strains are expected. However, when these differences result in replacement, deletion or insertion of amino acid residues at positions that do not affect the activity of enzyme, such sequences fall within the scope of the desensitized DDPS gene.

A desensitized DDPS gene can be obtained, for example, as follows. First, DNA containing a wild-type DDPS gene, or another DDPS gene having a mutation, is subjected to in vitro mutation, and this mutated DNA is ligated with a vector DNA compatible with the chosen host to prepare a recombinant DNA. The recombinant DNA is introduced into the host microorganisms to obtain transformants, and a transformant that is able to express a desensitized DDPS is selected. Alternatively, an in vitro mutation treatment can be performed on the vector DNA containing the wild-type DDPS gene, or another DDPS gene having a mutation. Then, the mutated DNA can be introduced into host microorganisms to obtain transformants, and a transformant that is able to express a desensitized DDPS can be selected from the transformants. Such a transformant also harbors the desensitized DDPS gene.

Furthermore, a microorganism that produces wild-type DDPS may be subjected to a mutation treatment which results in a mutant strain that produces a desensitized DDPS, and then a desensitized DDPS gene can be obtained from the mutant strain. Alternatively, if a microorganism which has been transformed with a recombinant DNA ligated with a wild-type gene is subjected to a mutation treatment to prepare a mutant strain producing a desensitized DDPS and then a recombinant DNA is collected from the mutant strain, a desensitized DDPS gene is created on that DNA.

Examples of agents for the in vitro mutation treatment of DNA include hydroxylamine and so forth. Hydroxylamine is a chemical mutation treatment agent that causes replacement of cytosine with thymine by changing cytosine into $N^4$-hydroxycytosine. When a microorganism itself is subjected to a mutation treatment, the treatment is performed with ultraviolet irradiation or a typically-used mutagenizing agent such as N-methyl-N'-nitro-N-nitrosoguanidine (NTG) and nitrous acid.

Bacteria from which the DNA containing a wild-type DDPS gene, or another DDPS gene containing a mutation, is derived, any of microorganisms belonging to the genus *Escherichia* may be used. Specifically, those mentioned in the literature of Neidhardt et al. (Neidhardt, F. C. et. al., *Escherichia coli* and *Salmonella Typhimurium*, American Society for Microbiology, Washington D.C., 1208, Table 1) can be used. For example, *E. coli* JM109 strain and MC1061 strain can be used. When a wild-type strain is used as the donor of DNA containing a DDPS gene, DNA containing a wild-type DDPS gene can be obtained.

Examples of the desensitized AK include AK enzymes that have been mutated to obtain the desensitization to the feedback inhibition by L-lysine. The AK derived from *Escherichia* bacteria, and the AKIII derived from *E. coli* are exemplary. Examples of the mutation that desensitizes the feedback inhibition by L-lysine in AKIII include:

(a) replacing the glycine residue at position 323 with another amino acid residue (aspartic acid, for example), (b) replacing the glycine residue at position 323 with another amino acid residue (aspartic acid, for example), and replacing the glycine residue at position 408 with another amino acid residue (aspartic acid, for example), (c) replacing the arginine residue at position 34 with another amino acid residue (cysteine, for example), and replacing the glycine residue at position 323 with another amino acid residue (aspartic acid, for example), (d) replacing the leucine residue at position 325 with another amino acid residue (phenylalanine, for example), (e) replacing the methionine residue at position 318 with another amino acid residue (isoleucine, for example), (f) replacing the methionine residue at position 318 with another amino acid residue (isoleucine, for example), and replacing the valine residue at position 349 with another amino acid residue (methionine, for example), (g) replacing the serine residue at position 345 with another amino acid residue (leucine, for example), (h) replacing the valine residue at position 347 with another amino acid residue (methionine, for example), (i) replacing the threonine residue at position 352 with another amino acid residue (isoleucine, for example), (j) replacing the threonine residue at position 352 with another amino acid residue (isoleucine, for example), and replacing the serine residue at position 369 with another amino acid residue (phenylalanine, for example), (k) replacing the glutamic acid residue at position 164 with another amino acid residue (lysine, for example), and (l) replacing the methionine residue at position 417 with another amino acid residue (isoleucine, for example), and replacing the cysteine residue at position 419 with another amino acid residue (tyrosine, for example). The positions are those in the E. coli AKIII amino acid sequence (see SEQ ID NO: 8 in International Publication No. WO95/16042), as counted from the N-terminus. Furthermore, a mutation which results in replacing the glycine residue at position 323 with another amino acid residue, for example aspartic acid, and replacing the methionine residue at position 318 with another amino acid residue, for example isoleucine can also be used (Japanese Patent Application Laid-open No. 10-113183). It is well known that differences may occur among amino acid sequences from different species or strains, although these differences may not affect activity, and an amino acid residue corresponding to the aforementioned specific amino acid residues can be easily recognized by those skilled in the art.

Other examples of the desensitized AK include a mutant-type AK derived from coryneform bacteria (Japanese Patent Application Laid-open No. 6-62866).

In order to obtain an *Escherichia* bacterium which contains a desensitized AK, for example, DNA that encodes the desensitized AK can be introduced into the *Escherichia* bacteria.

Examples of the DNA coding for a desensitized AK include DNA coding for a wild-type AK which includes a mutation which results in an AK which is desensitized to feedback inhibition by L-lysine.

Hereinafter, a method for obtaining DNA coding for a desensitized AK will be explained by exemplifying AKIII derived from *Escherichia* bacteria, although DNA encoding AK from other organisms can be similarly obtained. Furthermore, if a wild-type AK derived from another organism is a desensitized AK, DNA coding for it can be used as it is.

The DNA coding for wild-type AKIII is not particularly limited. For example, DNA coding for AKIII derived from an *Escherichia* bacterium, such as *E. coli*, can be used. Specifically, DNA coding for the amino acid sequence shown in International Publication No. WO95/16042 (see specifically SEQ ID NO: 8 of this publication, and the sequence of nucleotide numbers 584-1930 of SEQ ID NO: 7 in International Publication No. WO95/16042 can be used. AKIII from *E. coli* is encoded by the lysC gene.

Mutations such as those disclosed above will result in a DNA coding for a mutant-type AKIII Furthermore, slight differences in the amino acid sequences of AKIII among bacterial species and strains are expected. However, when these differences result in replacement, deletion or insertion of amino acid residues at positions that do not affect the activity of enzyme, such sequences fall within the scope of the mutant AKIII gene. For example, the nucleotide sequence of the wild-type lysC gene obtained in Example 2 mentioned hereinafter (International Publication No. WO95/16042, SEQ ID NO: 7) has differences in the sequence at 6 positions with respect to the already published nucleotide sequence of lysC of *E. coli* K-12 JC411 strain (Cassan M., Parsot, C., Cohen, G. N., and Patte, J. C., J. Biol. Chem., 261, 1052 (1986)), among which two of the differences provide different encoded amino acid residues (lysC of the JC411 strain provides replacement of the glycine residue at position 58 with a cysteine residue and replacement of the glycine residue at position 401 with an alanine residue in the amino acid sequence encoded by lysC shown in SEQ ID NO: 8 of International Publication No. WO95/16042 wherein the position is counted from the N-terminus thereof). It is expected that even lysC having the same sequence as lysC of the *E. coli* K-12 JC411 strain may provide lysC having a mutation that desensitizes the feedback inhibition by L-lysine, if it is introduced along with any of mutations mentioned in the above (a) to (l), or a mutation for replacing an amino acid residue corresponding to the glycine residue at position 323 with another amino acid residue (for example aspartic acid), and replacing an amino acid residue corresponding to the methionine residue at position 318 with another amino acid residue.

A DNA coding for a mutant-type AKIII that is desensitized to feedback inhibition by L-lysine can be obtained, for example, as follows. First, DNA containing a wild-type AKIII gene, or another AKIII gene having a mutation, is subjected to in vitro mutation, and this mutated DNA is ligated to a vector DNA compatible with a chosen host to prepare a recombinant DNA. The recombinant DNA can be introduced into the host microorganisms to obtain transformants, and a transformant that is able to express a mutant type AKIII can be selected. Alternatively, an in vitro mutation treatment can be performed on the vector DNA containing the wild-type AKIII, or another AKIII gene having a mutation. Then, the mutated DNA can be introduced into the host microorganisms to obtain transformants, and a transformant that is able to express a mutant-type AKIII can be selected from the transformants. Such a transformant also harbors the mutant type gene.

Furthermore, a microorganism that produces a wild-type enzyme may be subjected to a mutation treatment which results in a mutant strain that produces a mutant-type enzyme, and then the mutant-type gene can be obtained from the mutant strain. Examples of agents for directly subjecting DNA to a mutation treatment include hydroxylamine and so forth. Hydroxylamine is a chemical mutation treatment agent that causes replacement of cytosine with thymine by changing cytosine into $N^4$-hydroxycytosine. When a microorganism itself is subjected to a mutation treatment, the treatment is performed with ultraviolet irradiation or a mutagenizing agent usually used for artificial mutation such as N-methyl-N'-nitro-N-nitrosoguanidine (NTG).

Bacteria from which the DNA containing a wild-type AKIII gene, or another AKIII gene having a mutation, is derived, any of microorganisms belonging to the genus Escherichia may be used. Specifically, those mentioned in the literature of Neidhardt et al. (Neidhardt, F. C. et. al., *Escherichia coli* and *Salmonella Typhimurium*, American Society for Microbiology, Washington D.C., 1208, Table 1) can be used. For example, *E. coli* JM109 strain, MC1061 strain and so forth can be used.

Aspartokinase, dihydrodipicolinate reductase, tetrahydrodipicolinate succinylase, succinyl diaminopimelate deacylase, phosphoenolpyruvate carboxylase, and aspartate-semialdehyde dehydrogenase each can be derived from *Escherichia* bacteria; nicotinamide adenine dinucleotide transhydrogenase and aspartase, if present, can each be derived from *Escherichia* bacteria; dihydrodipicolinate synthase can be derived from an *Escherichia* bacterium or *Brevibacterium* bacterium, and diaminopimelate dehydrogenase can be derived from a *Brevibacterium* bacterium.

Examples of the *Brevibacterium* bacteria include *Brevibacterium lactofermentum, Brevibacterium flavum, Brevibacterium divaricatum, Corynebacterium glutamicum, Corynebacterium lilium*, and so forth.

Furthermore, the intracellular activities of dihydrodipicolinate synthase and aspartokinase are enhanced by the use of feedback-desensitized dihydrodipicolinate synthase and aspartokinase, and the intracellular activity of diaminopimelate dehydrogenase can be enhanced by introduction of a diaminopimelate dehydrogenase gene. Such bacteria may be obtained by introducing the plasmid pCABD2 or pCABDE1 (see International Publication No. WO95/16042) into an *Escherichia* bacterium.

<2> Production Method of the Present Invention

L-Lysine can efficiently be produced by culturing the bacteria as described above in a suitable medium to produce and accumulate L-lysine in the culture, and collecting the L-lysine from the culture.

The medium used for the culture of the bacteria may be a typical medium which includes a carbon source, a nitrogen source, inorganic ions, and other organic trace nutrients as required.

As the carbon source, sugars such as glucose, lactose, galactose, fructose and starch hydrolysate; alcohols such as glycerol and sorbitol; or organic acids such as fumaric acid, citric acid and succinic acid can be used.

As the nitrogen source, inorganic ammonium salts such as ammonium sulfate, ammonium chloride or ammonium phosphate; organic nitrogen such as soybean hydrolysate; ammonia gas; or aqueous ammonia can be used.

As for the organic trace nutrients, required substances such as vitamin $B_1$ and L-isoleucine, yeast extract and so forth can be added in a suitable amount. In addition to these, a small amount of potassium phosphate, magnesium sulfate, iron ions, manganese ions and so forth can be added.

Culture can be carried out under aerobic conditions for 16-72 hours. The culture temperature can be controlled to be 20° C. to 45° C., and the pH can be controlled to be 5 to 8 during the culture. Inorganic or organic, acidic or alkaline substances as well as ammonia gas and so forth can be used to adjust the pH.

Collection of L-lysine from the fermented liquor is usually carried out by a combination of an ion exchange resin method, a precipitation method, and other known techniques.

EXAMPLES

The present invention will be further specifically explained hereinafter with reference to the following examples.

Example 1

<1> Preparation of *Escherichia* Bacteria Having Various Properties

The plasmids shown below were introduced into *E. coli* W3110 (tyrA).

| Name of plasmid | gene(s) on plasmid |
| --- | --- |
| RSF24P | dapA* |
| RSFD80 | dapA*, lysC* |
| pCAB1 | dapA*, lysC*, dapB |
| pCABD2 | dapA*, lysC*, dapB, ddh |
| pCABD(B) | Brev. dapA, lysC*, dapB, ddh |
| pCABDE1 | dapA*, lysC*, dapB, dapD, dapE |

The abbreviations used for the genes encode the following proteins.

ppc: Phosphoenolpyruvate carboxylase
lysC: Aspartokinase III
lysC*: Aspartokinase III desensitized to inhibition
asd: Aspartate-semialdehyde dehydrogenase
dapA: Dihydrodipicolinate synthase
dapA*: Dihydrodipicolinate synthase desensitized to inhibition
Brev. dapA: Dihydrodipicolinate synthase desensitized to inhibition (derived from *Brevibacterium lactofermentum*)
dapB: Dihydrodipicolinate reductase
dapD: Tetrahydrodipicolinate succinylase
dapE: Succinyl diaminopimelate deacylase
ddh: Diaminopimelate dehydrogenase (derived from *Brevibacterium lactofermentum*)

The plasmids RSF24P, RSFD80, pCAB1, pCABD2, and pCABDE1 are described in International Publication No. WO95/16042. The constructions thereof are also described in International Publication No. WO95/16042, and outlined below.

(1) RSF24P

Based on the known dapA nucleotide sequence of *E. coli* (J. Bacteriol., 166, 297 (1986)), a fragment containing the SD sequence and open reading frame (ORF) of dapA was amplified by PCR. The amplified fragment was ligated to the cloning vector pCR1000 to obtain the plasmid pdapA2, in which dapA was ligated so that the transcription direction of dapA was reverse to the transcription direction by the lacZ promoter in pCR1000. The plasmid pdapA2 was subjected to a mutagenesis treatment by using hydroxylamine, and pdapA2 subjected to the mutagenesis treatment was introduced into *E. coli* W3110. From the transformants, those exhibiting AEC resistance were selected. Furthermore, the degree of the inhibition by L-lysine of DDPS encoded by the plasmids harbored by the selected resistant strains was measured, and a strain that was desensitized to the inhibition by L-lysine was selected. The plasmid pdapA24, which was confirmed to have the change at 597th C to T by sequencing, was ligated to pVIC40 at a position downstream from the tetracycline resistance gene promoter to obtain RSF24P (FIG. 1).

An *E. coli* JM109 strain into which RSF24P was introduced was designated as AJ12395, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 28, 1993 and received an accession number of FERM P-13935. Then, it was converted to an international deposit under the provisions of the Budapest Treaty on Nov. 1, 1994, and received an accession number of FERM BP-4858.

(2) RSFD80

Figure 2:
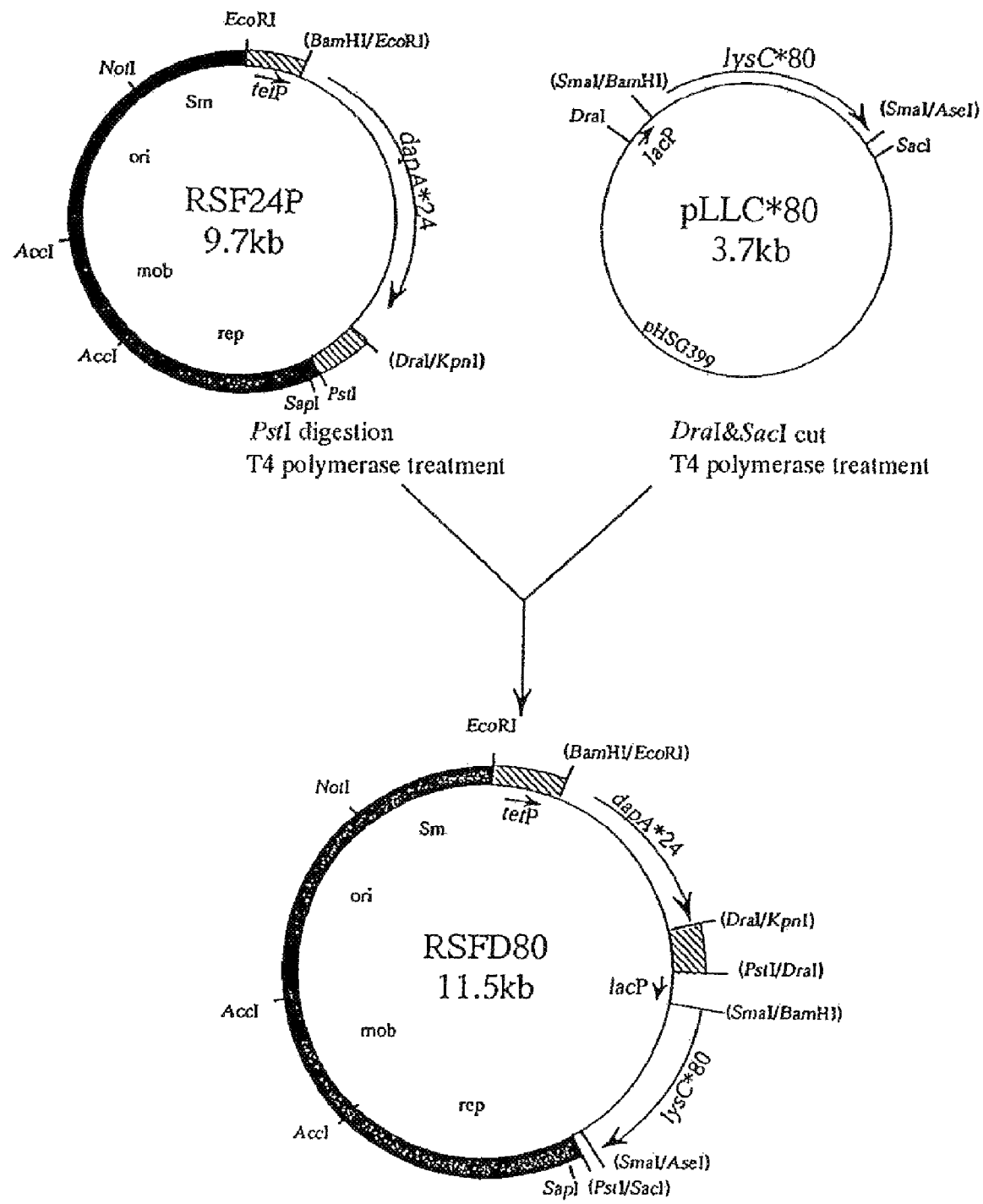
FIG. 2 shows a process of producing the plasmid RSFD80 containing dapA*24 and lysC*80.

Based on the known lysC nucleotide sequence of *E. coli* (J. Biol. Chem., 261, 1052 (1986)), a fragment containing the SD sequence and ORF of lysC was amplified by PCR. The amplified fragment was ligated to the multi-copy vector pUC18 to obtain the plasmid pLYSC1, in which lysC was ligated so that the transcription direction of lysC was reverse to the transcription direction by the lacZ promoter in pUC18. The plasmid pLYSC1 was subjected to a mutagenesis treatment by using hydroxylamine, and pLYSC1 subjected to the mutagenesis treatment was introduced into *E. coli* GT3. From the transformants, those exhibiting AEC resistance and L-lysine resistance were selected. Furthermore, pLYSC1 was introduced into *E. coli* MC1061, then the cells were subjected to a mutagenesis treatment by using hydroxylamine, and those exhibiting AEC resistance and L-lysine resistance were selected. Furthermore, the degree of the inhibition by L-lysine and thermal stability of AK encoded by the plasmids harbored by the selected resistant strains were measured, and a strain which was desensitized to the inhibition by L-lysine and which exhibited superior stability was selected. The plasmid pLYSC1*80, which was confirmed to have the change at 352nd C to T by sequencing, was ligated to pHSG399 at a position downstream from the lacZ promoter to obtain pLLC*80. From pLLC*80 and RSF24P, RSFD80 was constructed as shown in FIG. 2.

An *E. coli* JM109 strain into which RSFD80 was introduced was designated as AJ12396, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 28, 1993 and received an accession number of FERM P-13936. Then, it was converted to an international deposition under the provisions of the Budapest Treaty on Nov. 1, 1994, and received an accession number of FERM BP-4859.

(3) pCAB1

Figure 3:
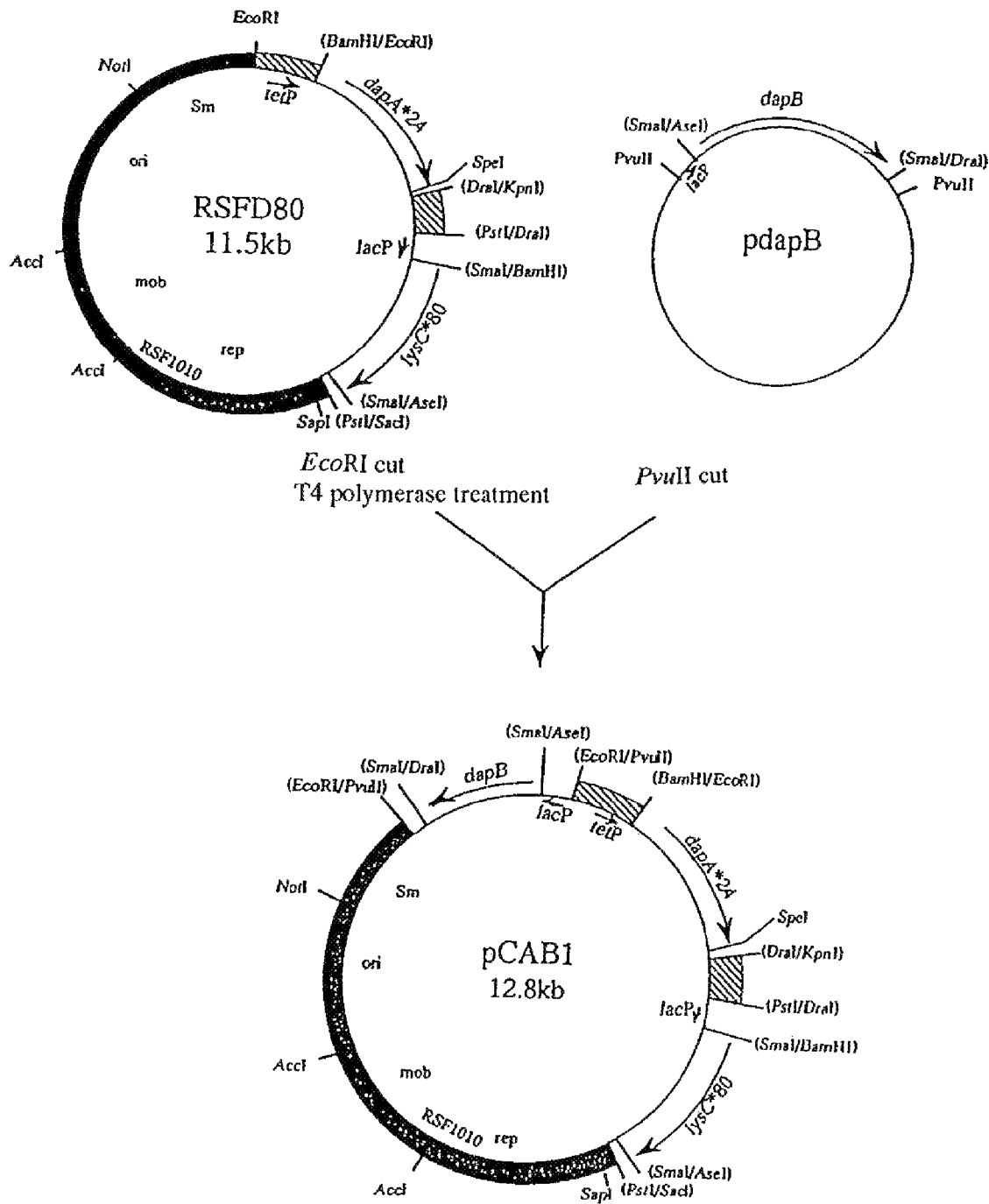
FIG. 3 shows a process of producing the plasmid pCAB1 containing dapA*24, lysC*80, and dapB.

Based on the known dapB nucleotide sequence (Bouvier, J. et al., J. Biol. Chem., 259, 14829 (1984)), dapB was amplified from *E. coli* W3110 strain chromosomal DNA by PCR. The obtained amplified DNA fragment was digested with AseI and DraI, and the obtained fragment was blunt-ended and inserted into the SmaI site of pMW119 to obtain a plasmid pdapB. Subsequently, dapB was introduced into RSFD80 as shown in FIG. 3 to obtain pCAB1.

(4) pCABD2

Figure 4:
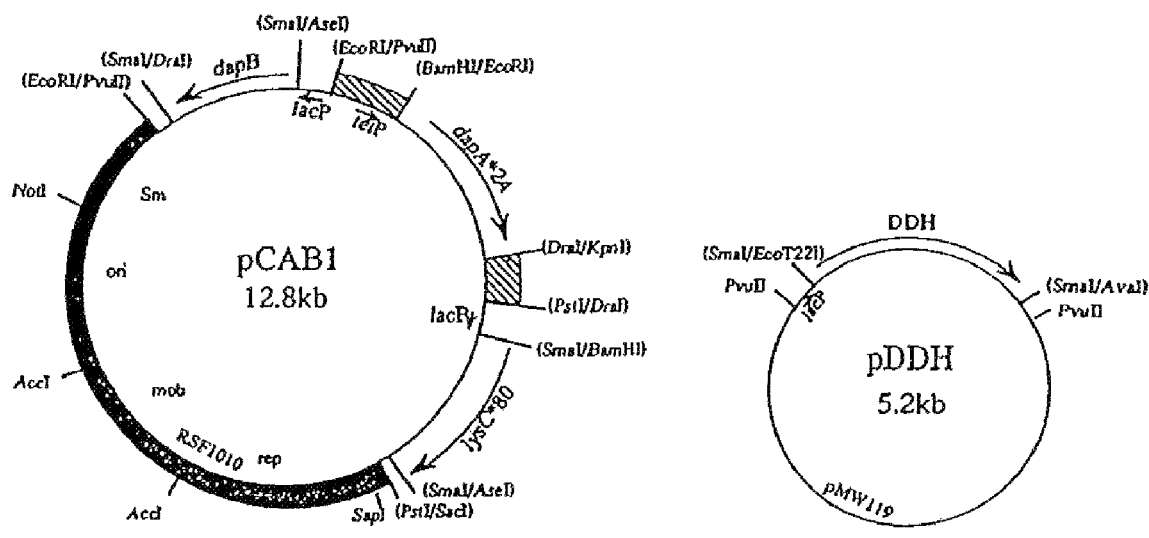
FIG. 4 shows a process of producing the plasmid pCABD2 containing dapA*24, lysC*80, dapB, and ddh.
Figure 4:
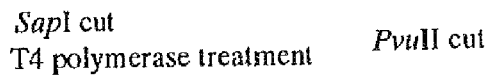
Figure 4:
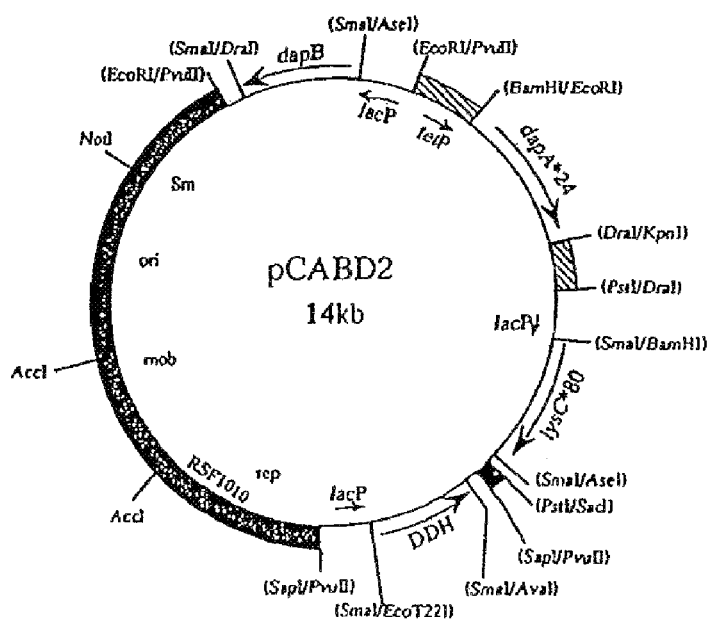

Based on the known ddh nucleotide sequence of *Corynebacterium glutamicum* (Ishino, S. et al., Nucleic Acids Res., 15, 3917 (1987)), ddh was amplified from chromosomal DNA of *Brevibacterium lactofermentum* ATCC13869 by PCR. The obtained amplified DNA fragment was digested with EcoT22I and AvaI, and the obtained fragment was blunt-ended and inserted into the SmaI site of pMW119 to obtain a plasmid pddh. Subsequently, ddh was introduced into pCAB1 as shown in FIG. 4 to obtain a plasmid pCABD2.

(5) pCABDE1

Figure 5:
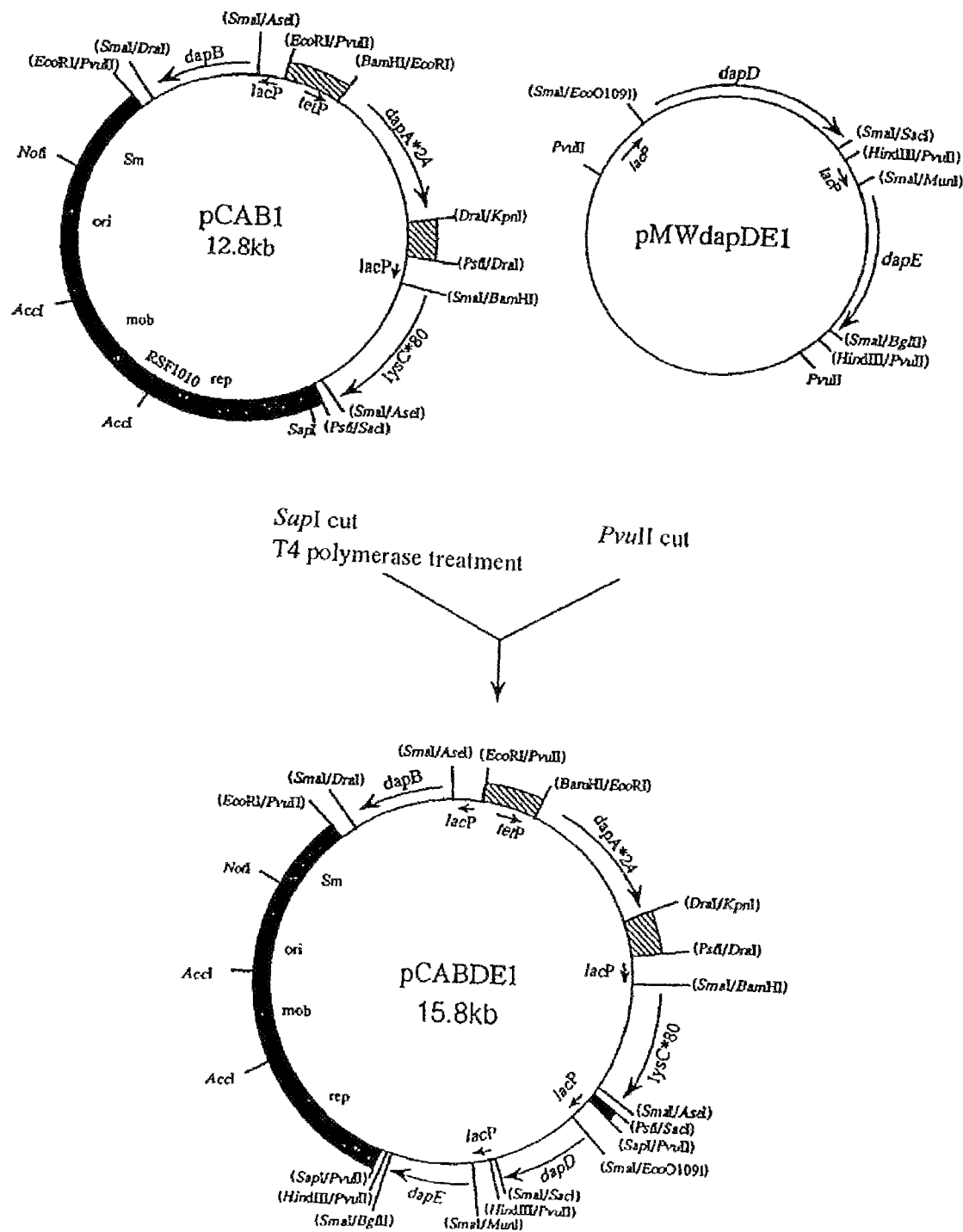
FIG. 5 shows a process of producing the plasmid pCABDE1 containing dapA*24, lysC*80, dapB, dapD, and dapE.
Figure 6:
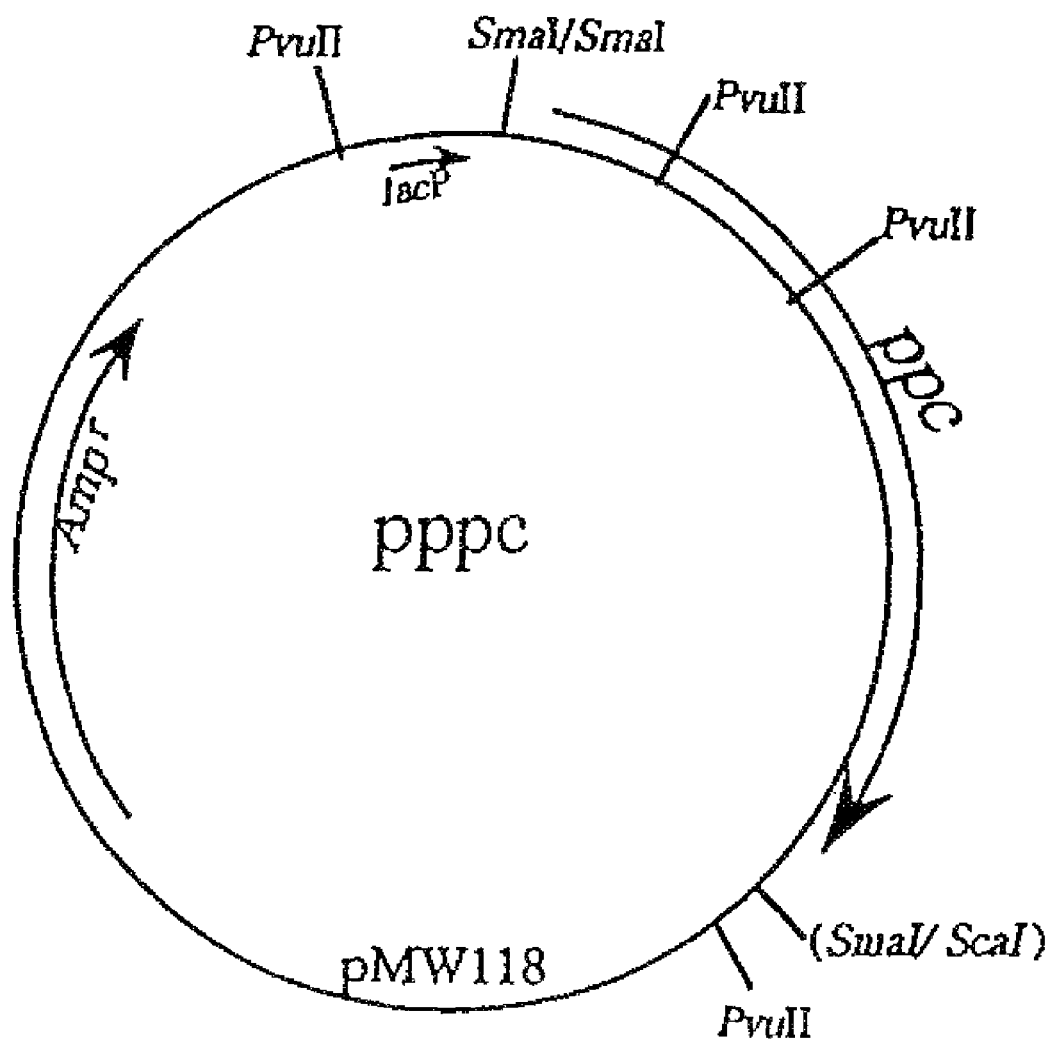
FIG. 6 shows the structure of plasmid pppc containing ppc.
Figure 7:
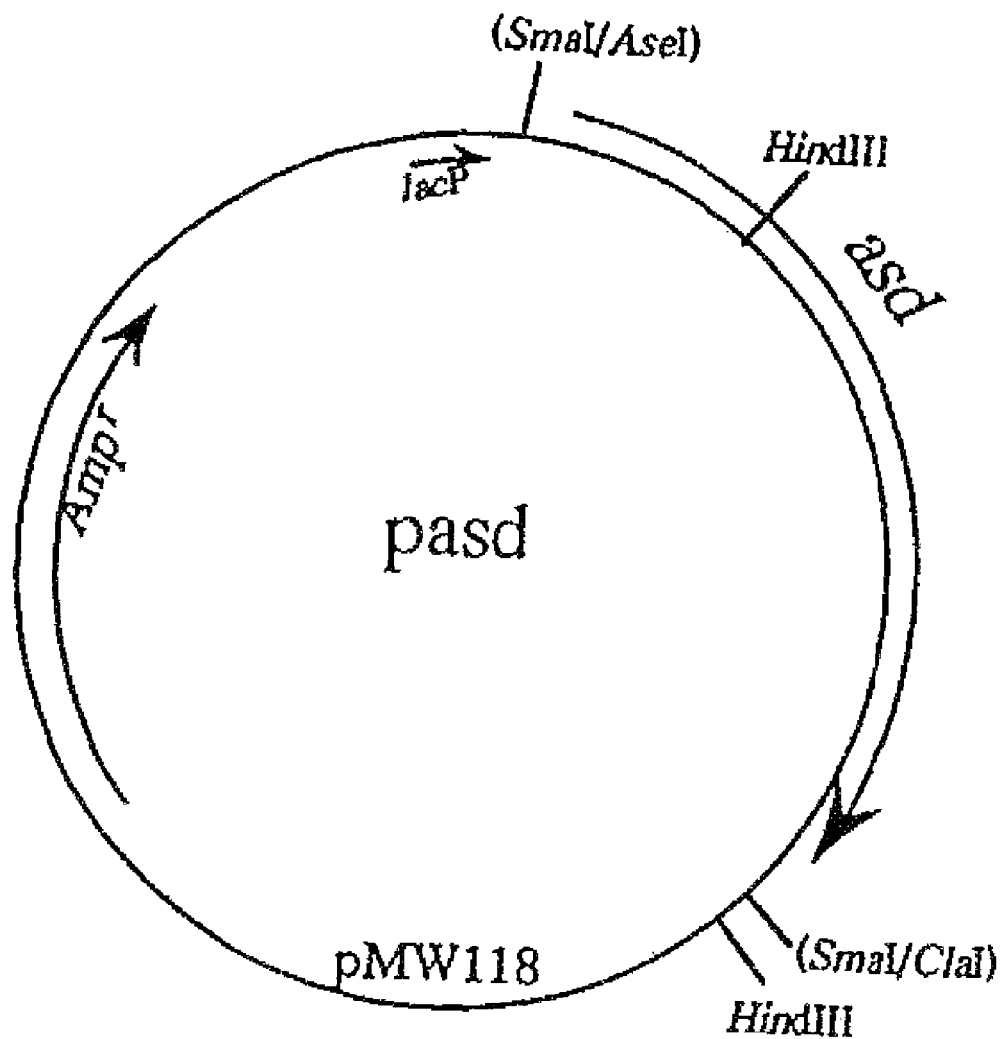
FIG. 7 shows the structure of plasmid pasd containing asd.

Based on the known dapD nucleotide sequence (Richaud, C. et al., J. Biol. Chem., 259, 14824 (1984)), dapD was amplified from chromosomal DNA of *E. coli* W3110 strain by PCR. The obtained amplified DNA fragment was digested with EcoO1091 and SadI, and the obtained fragment was blunt-ended and inserted into the SmaI site of pMW118 to obtain a plasmid pdapD. Furthermore, based on the known dapE nucleotide sequence (Bouvier, J. et al., J. Bacteriol., 174, 5265 (1992)), dapE was amplified from chromosome DNA of *E. coli* W3110 strain by PCR. The obtained amplified DNA fragment was digested with MunI and BglII, and an obtained fragment was blunt-ended and inserted into the SmaI site of pMW118 to obtain a plasmid pdapE. Furthermore, dapE was excised from pdapE and inserted into pdapD to obtain a plasmid pMWdapDE1 containing both of dapE and dapD. As shown in FIG. 5, a fragment containing dapE and dapD was excised from pMWdapDE1, and inserted into pCAB1 to obtain pCABDE1.

A plasmid pCABD(B) was constructed as follows.

First, a DNA fragment containing the promoter site of Tet resistance gene was amplified from pBR322 by using primers having the following sequences:

```
5'-TCAAGAATTCTCATGTTTGA-3'          (SEQ ID NO: 1)

5'-GTTAGATTTGGTACCCGGTGCCTGACTGCGTTA (SEQ ID NO: 2)
GC-3'
```

Figure 18:
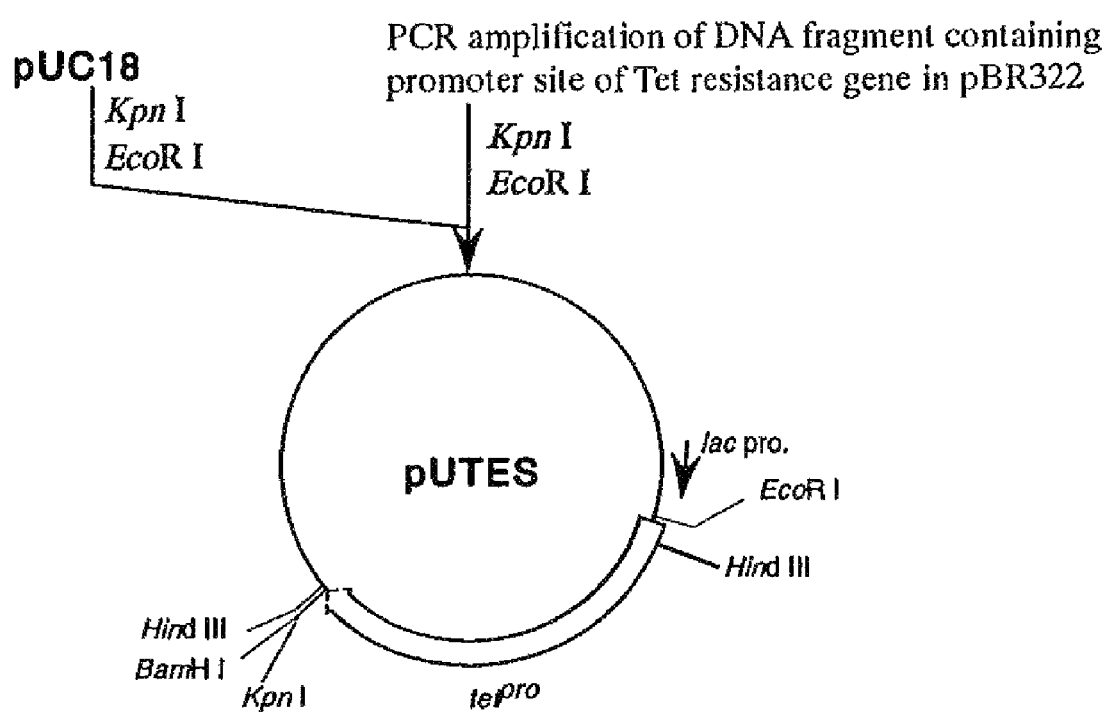
FIG. 18 shows a process of producing the plasmid pUTES containing tet$^{pro}$.

The amplified DNA fragment was digested with KpnI and EcoRI, and inserted between KpnI and EcoRI cleavage sites of pUC18 to obtain pUTES (FIG. 18).

Then, the Brev. dapA gene was amplified by using chromosomal DNA of *Brevibacterium lactofermentum* Ysr strain as a template and the primers having the following sequences:.

```
5'-GGTTGTGGTACCCCCAAATGAGGGAAGAAG-3' (SEQ ID NO: 3)

5'-TGGAACCTCTGTTGCTGCAG-3'          (SEQ ID NO: 4)
```

Figure 19:
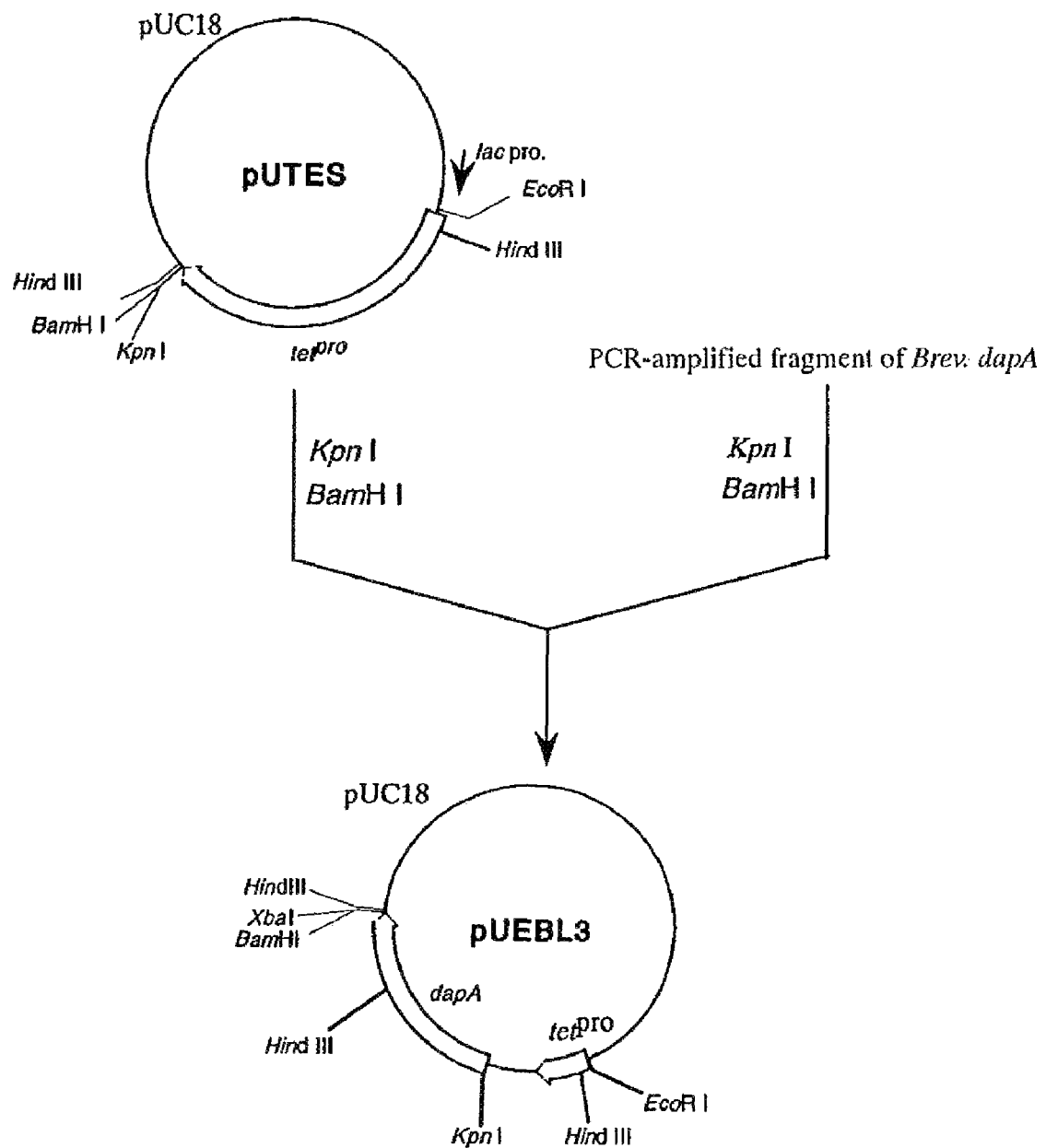
FIG. 19 shows a process of producing the plasmid pUEBL3 containing tet$^{pro}$, and dapA from *Brevibacterium lactofermentum*, which is located downstream from tet$^{pro}$.

The amplified Brev. dapA gene was digested with KpnI and BamHI, and inserted between KpnI and BamHI cleavage sites of pUTES to obtain pUEBL3 (FIG. 19).

Figure 20:
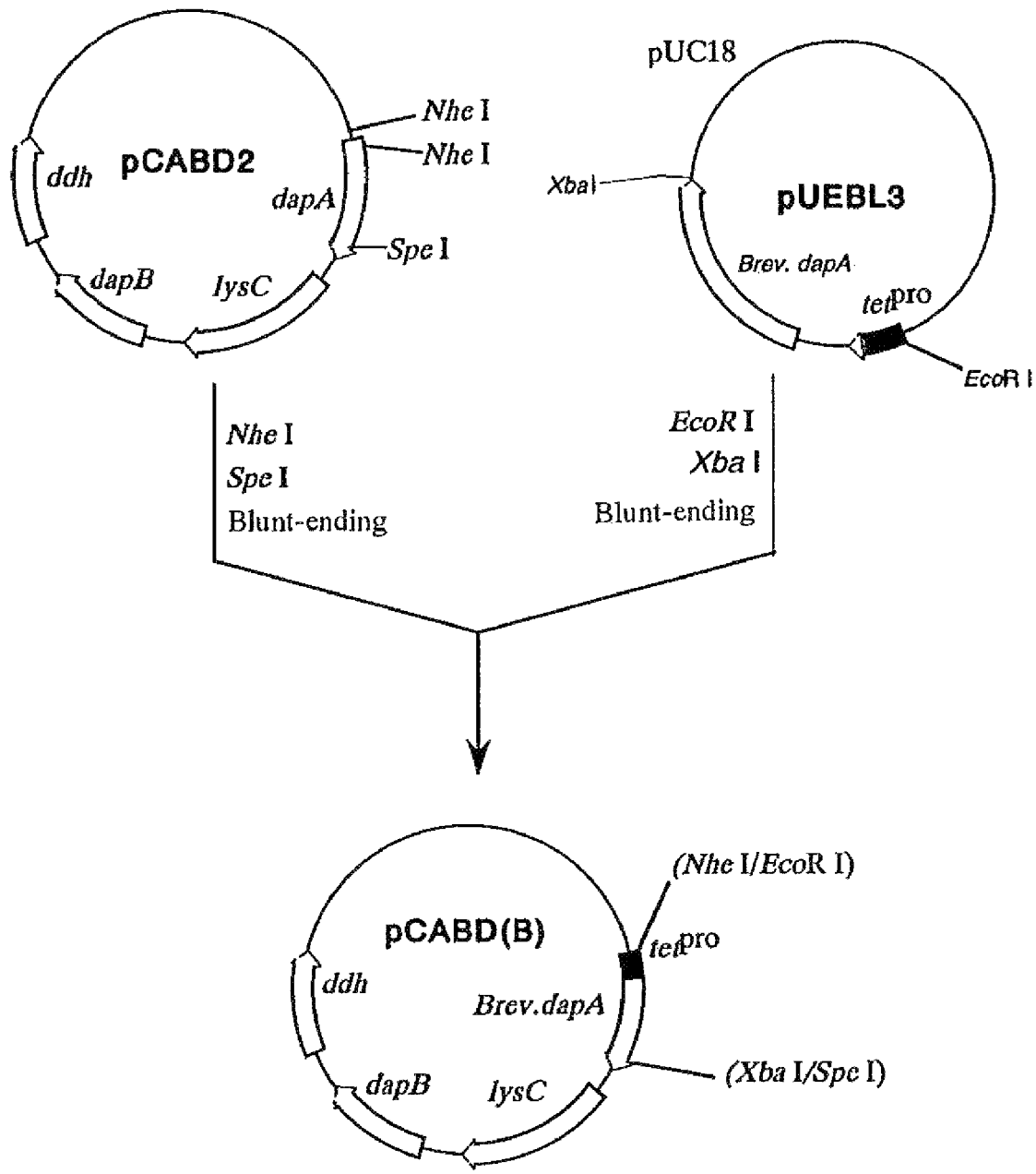
FIG. 20 shows a process of producing the plasmid pCABD (B) containing dapA from *Brevibacterium lactofermentum* (Brev. dapA), lysC, dapB, and ddh.

Then, pUEBL3 was digested with EcoRI and XbaI, and blunt-ended for the both ends to obtain a fragment containing Brev. dapA. Thereafter, pCABD2 (see International Publication No. WO95/16042) was digested with NheI and SpeI and blunt-ended for the both ends. A fragment containing lysC, dapB and ddh was collected, and then the previously obtained fragment containing Brev. dapA was inserted thereto to obtain pCABD(B) (FIG. 20)

While *E. coli* W3110 (tyrA) is detailed in European Patent Publication No. 488-424, the preparation method therefor will be briefly explained below. The *E. coli* W3110 strain was obtained from the National Institute of Genetics (Shizuoka-ken, Mishima-shi). This strain was inoculated on an LB plate containing streptomycin, and a strain that formed a colony was selected to obtain a streptomycin resistant strain. The selected streptomycin resistant strain and *E. coli* K-12 ME8424 strain were mixed and cultured in a complete medium (L-Broth: 1% Bacto trypton, 0.5% Yeast extract, 0.5% NaCl) as stationary culture at 37° C. for 15 minutes to induce conjugation. The *E. coli* K-12 ME8424 strain has genetic traits of HfrPO45, thi, relA1, tyrA::Tn10, ung-1 and nadB, and can be obtained from the National Institute of Genetics.

Then, the culture was inoculated to a complete medium (L-Broth: 1% Bacto trypton, 0.5% yeast extract, 0.5% NaCl, 1.5% agar) containing streptomycin, tetracycline and L-tyrosine, and a strain that formed a colony was selected. This strain was designated as *E. coli* W3110 (tyrA) strain.

Many strains formed by introducing a plasmid into the W3110 (tyrA) strain are disclosed in European Patent Publication No. 488-424. For example, a strain obtained by introducing a plasmid pHATerm was designated as *E. coli* W3110 (tyrA)/pHATerm strain (*E. coli* AJ12662 strain), and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Nov. 16, 1991 as an international deposit and received an accession number of FERM BP-3653. The W3110 (tyrA) strain can also be obtained by eliminating the plasmid pHATerm from this *E. coli* W3110 (tyrA)/pHATerm strain. The elimination of the plasmid can be performed in a conventional manner.

<2> Introduction of Aspartate-Semialdehyde Dehydrogenase Gene (asd), Phosphoenolpyruvate Gene (ppc) or Aspartase Gene (aspa), and Evaluation of L-Lysine Productivity As a plasmid containing asd and a plasmid containing ppc, pasd and pppc (see International Publication No. WO95/16042) were used. Constructions of these plasmids were detailed in International Publication No. WO95/16042. The outlines are as follows.

(1) pasd

Figure 8:
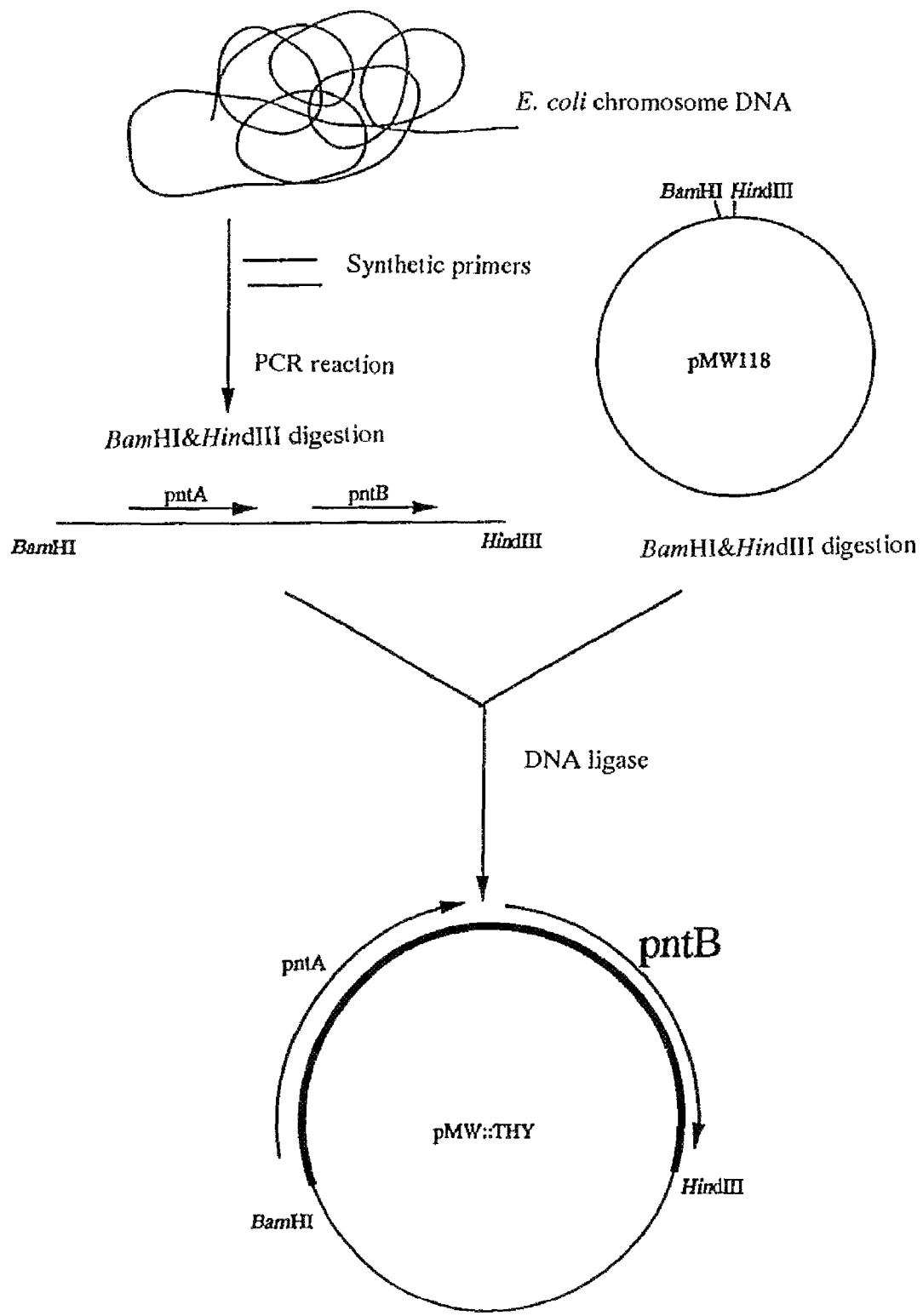
FIG. 8 shows a process of producing the plasmid pMW::THY containing pntAB (pntA and pntB).

The plasmid asd was obtained from a plasmid pAD20 (Haziza, C. et al., EMBO, 1, 379 (1982)), which contained the gene. The plasmid pAD20 was digested with AseI and ClaI, blunt-ended and inserted into the SmaI site of pMW118 to obtain a plasmid pasd (FIG. 8).

(2) pppc

Figure 9:
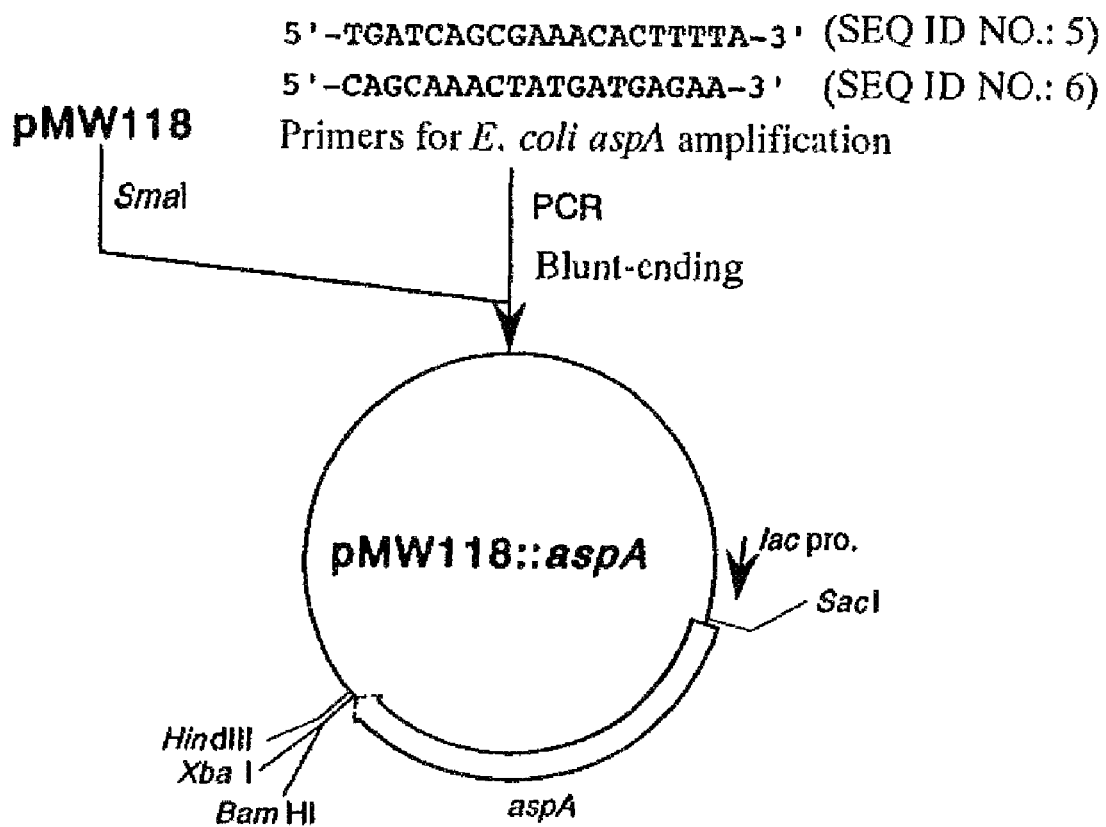
FIG. 9 shows a process of producing the plasmid pMW118::aspA containing aspA.

The plasmid pppc was obtained from a plasmid pT2 that contained the gene. The plasmid pT2 was digested with SmaI and ScaI, blunt-ended, and inserted into the SmaI site of pMW118 to obtain the plasmid pppc (FIG. 9). An *E. coli* F15 strain (AJ12873) harboring pT2 was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Jul. 15, 1993 and received an accession number of FERM P-13752. Then, it was converted to an international deposit under the provisions of the Budapest Treaty on Jul. 11, 1994, and received an accession number of FERM BP-4732.

A plasmid containing aspA was constructed as follows.

The aspA gene of *E. coli* was amplified by using primers having the following sequences:

```
5'-TGATCAGCGAAACACTTTTA-3'    (SEQ ID NO: 5)

5'-CAGCAAACTATGATGAGAA-3'     (SEQ ID NO: 6)
```

Then, the obtained amplified fragment was inserted into the SmaI cleavage site of pMW118 (Nippon Gene) to obtain pMW118::aspA (FIG. 9).

Each of pMW118 (control plasmid), pasd, pppc and pMW118::aspA (comparative plasmid) was introduced into each of *E. coli* W3110 (tyrA) and the transformants obtained in the aforementioned <1>. The obtained transformants, except for those obtained by introducing pMW118, pasd, pppc or pMW118::aspA into *E. coli* W3110 (tyrA), contained two kinds of plasmids, i.e. one of pMW118, pasd, pppc and pMW118::aspA and one of RSF24P, RSFD80, pCAB1, pCABD2, pCABD(B) and pCABDE1. These transformants were examined for L-lysine productivity by the method described in International Publication No. WO95/16042. The specific procedure was as follows.

The cells were cultured in 20 ml of a medium having the following composition contained in a 500-ml Sakaguchi flask at a temperature of 37° C. for 30 hours with stirring at 114-116 rpm.

Medium Composition:

| | |
|---|---|
| Glucose | 40 g/l |
| $MgSO_4 \cdot 7H_2O$ | 1 g/l |
| $(NH_4)_2SO_4$ | 16 g/l |
| $KH_2PO_4$ | 1 g/l |
| $FeSO_4 \cdot 7H_2O$ | 0.01 g/l |
| $MnSO_4 \cdot 5H_2O$ | 0.01 g/l |
| Yeast Extract (Difco) | 2 g/l |
| L-Tyrosine | 0.1 g/l |

Adjusted to pH 7.0 with KOH, and autoclaved at 115° C. for 10 minute (glucose and $MgSO_4.7H_2O$ were separately sterilized).

| | |
|---|---|
| $CaCO_3$ | 25 g/l |

(according to the Pharmacopoeia of Japan, sterilized by dry heat at 180° C. for 2 days)

Antibiotic (20 mg/l of streptomycin, 50 mg/l of ampicillin or 25 mg/l of kanamycin depending on the kind of the plasmid to be introduced)

L-Lysine in the culture broth (medium after the culture) was quantified by using Biotech Analyzer AS210 produced by Asahi Chemical Industry Co., Ltd.

The results are shown in Table 1. In the table, the amount of L-lysine is indicated in terms of mg per dl of the medium.

TABLE 1

| | Lys accumulation (mg/dl) | | | |
|---|---|---|---|---|
| | pMW118 | pasd | pppc | pMW118::aspA |
| — | 40 | 50 | 60 | 60 |
| RSF24P | 350 | 340 | 360 | 350 |
| RSFD80 | 960 | 790 | 990 | 960 |
| pCAB1 | 1120 | 1140 | 1150 | 1130 |
| PCABD2 | 1230 | 1320 | 1380 | 1240 |
| pCABD(B) | 1230 | 1320 | 1370 | n.d. |
| PCABDE1 | 1210 | 1310 | 1350 | n.d. | n.d.: Not determined

As clearly seen from the results shown in Table 1, when asd or ppc was enhanced each alone or together with dapA (RSF24P), dapA+lysC(RSFD80) or dapA+lysC+dapB (pCAB1) in *E. coli*, the production amount of L-lysine (accumulated amount) was not changed or only slightly changed and, as for asd, it might be reduced compared with the case where asd or ppc was not enhanced (−180 to 20 mg/dl as for asd, 10 to 30 mg/dl as for ppc). In contrast, if they were enhanced together with dapA+lysC+dapB+ddh (pCABD2) or dapA+lysC+dapB+dapD+dapE (pCABDE1), a marked increase of the L-lysine production amount was observed compared with when asd or ppc was not enhanced (70 mg/dl as for asd, 90 mg/dl as for ppc). However, when aspA was enhanced with dapA+lysC+dapB+ddh (pCABD2), a marked increase of the L-lysine production amount was not observed. Furthermore, even when dapA derived from *Brevibacterium lactofermentum* was used instead of dapA derived from

*Escherichia coli* (pCABD (B)), the same effect was obtained as when dapA derived from *Escherichia coli* was used (pCABD2). Therefore, the origin of the genes is not considered important, but the combination thereof is important.

Example 2

<1> Construction of Plasmids Containing Phosphoenolpyruvate Carboxylase Gene (ppc) and Aspartate-Semialdehyde Dehydrogenase Gene (asd), Transhydrogenase Gene (pntab) or Aspartase Gene (aspA)

A plasmid containing ppc and asd, a plasmid containing ppc and pntAB, and a plasmid containing ppc and aspA were constructed as follows.

(1) Plasmid Containing ppc and asd (ppcd)

Figure 10:
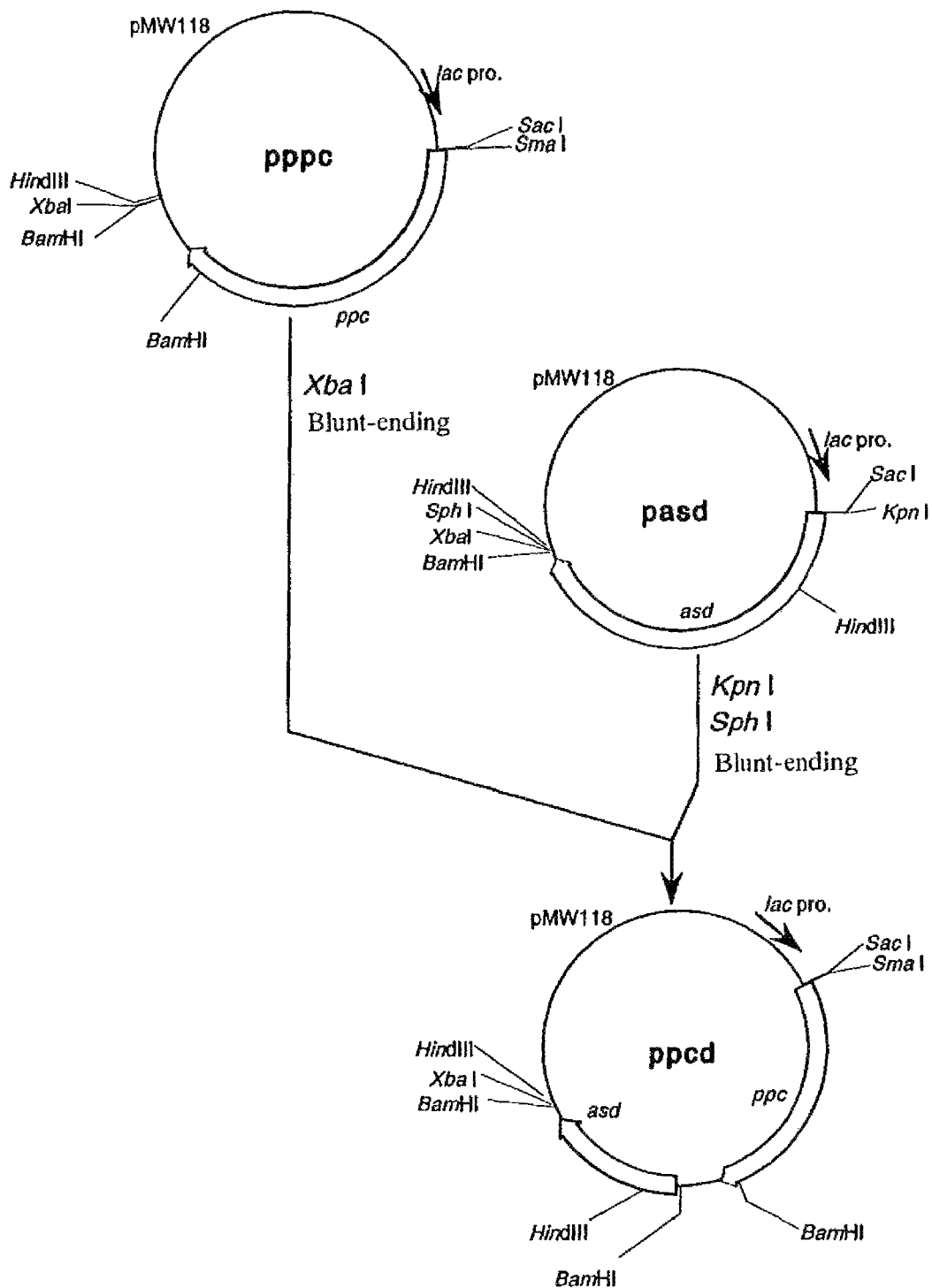
FIG. 10 shows a process of producing the plasmid ppcd containing ppc and asd.

The plasmid pasd disclosed in International Publication No. WO95/16042 was digested with KpnI and SphI, and the DNA fragment containing asd was blunt-ended for the both ends. Then, pppc disclosed in International Publication No. WO95/16042 was digested with XbaI and blunt-ended for the both ends, and the previously obtained asd fragment was inserted thereto to obtain ppcd (FIG. 10).

(2) Plasmid Containing ppc and pntAB (pPTS)

Figure 11:
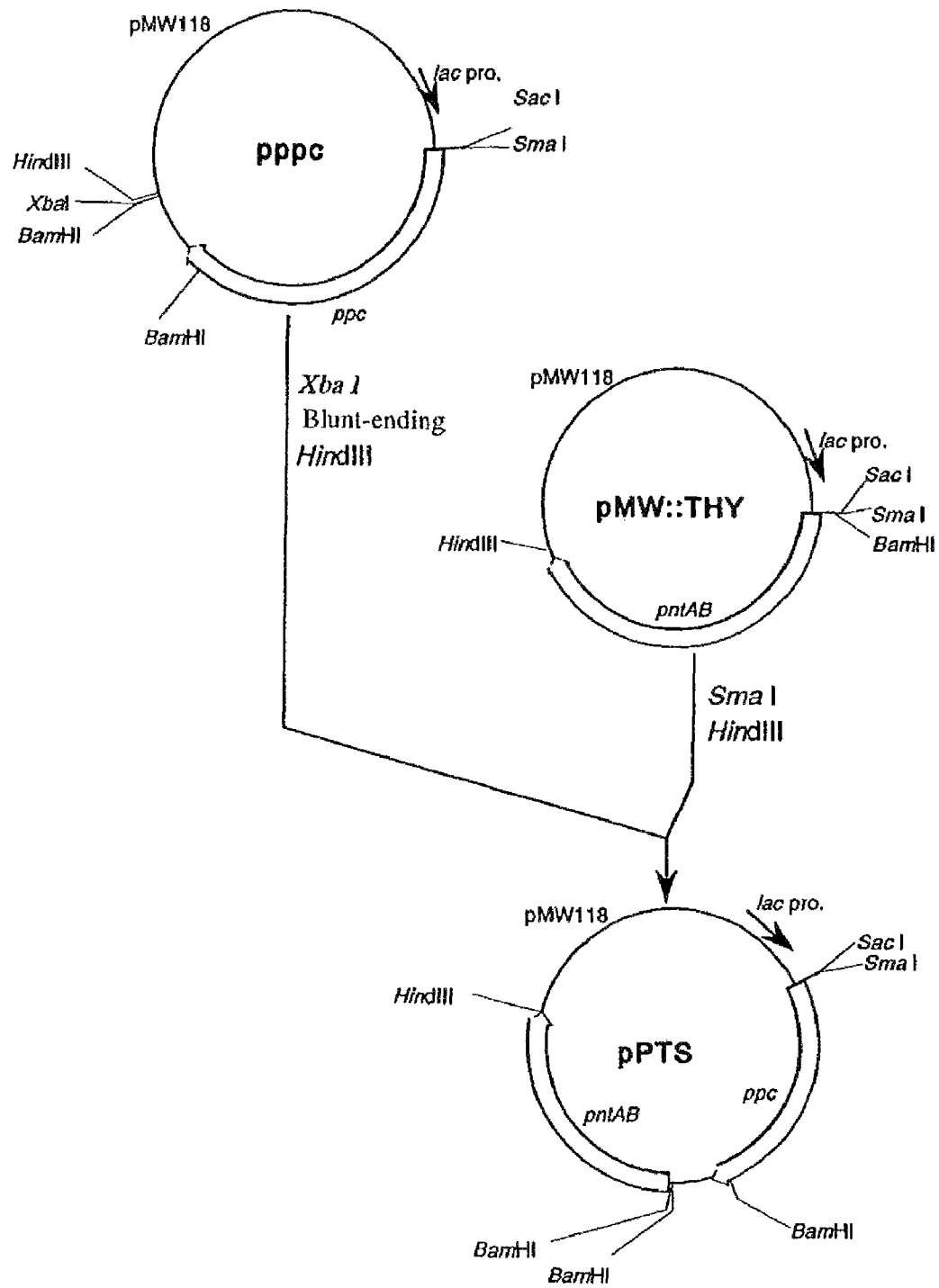
FIG. 11 shows a process of producing the plasmid pPTS containing ppc and pntAB.

The plasmid pMW::THY disclosed in International Publication No. WO95/11985 was digested with SmaI and HindIII, and the DNA fragment containing pntAB was collected. Then, pppc disclosed in International Publication No. WO95/16042 was digested with XbaI, blunt-ended for the both ends and further digested with HindIII, and the previously obtained pntAB fragment was inserted at the cleaved site to obtain pPTS (FIG. 11).

Construction of the plasmid pMW::THY is detailed in International Publication No. WO95/11985. It will be outlined below.

Based on the known pntA and pntB nucleotide sequences of *E. coli* (D. M. Clarke et al., Eur. J. Biochem., 158, 647-653 (1986)), a fragment containing both genes including regions having promoter activity was amplified by PCR. The amplified DNA fragment was digested with BamHI and HindIII, and the obtained DNA fragment was ligated to the plasmid vector pMW118 (Nippon Gene) digested with BamHI and HindIII to obtain pMW::THY (FIG. 8).

The *E. coli* JM109 strain into which pMW118::THY was introduced was designated as AJ12929, and it was deposited at the National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 4, 1993, and received an accession number of FERM P-13890. Then, it was transferred to an international deposit under the provisions of the Budapest Treaty on Sep. 14, 1994, and received an accession number of FERM BP-4798.

(3) Plasmid Containing ppc and aspA (pAPW)

Figure 12:
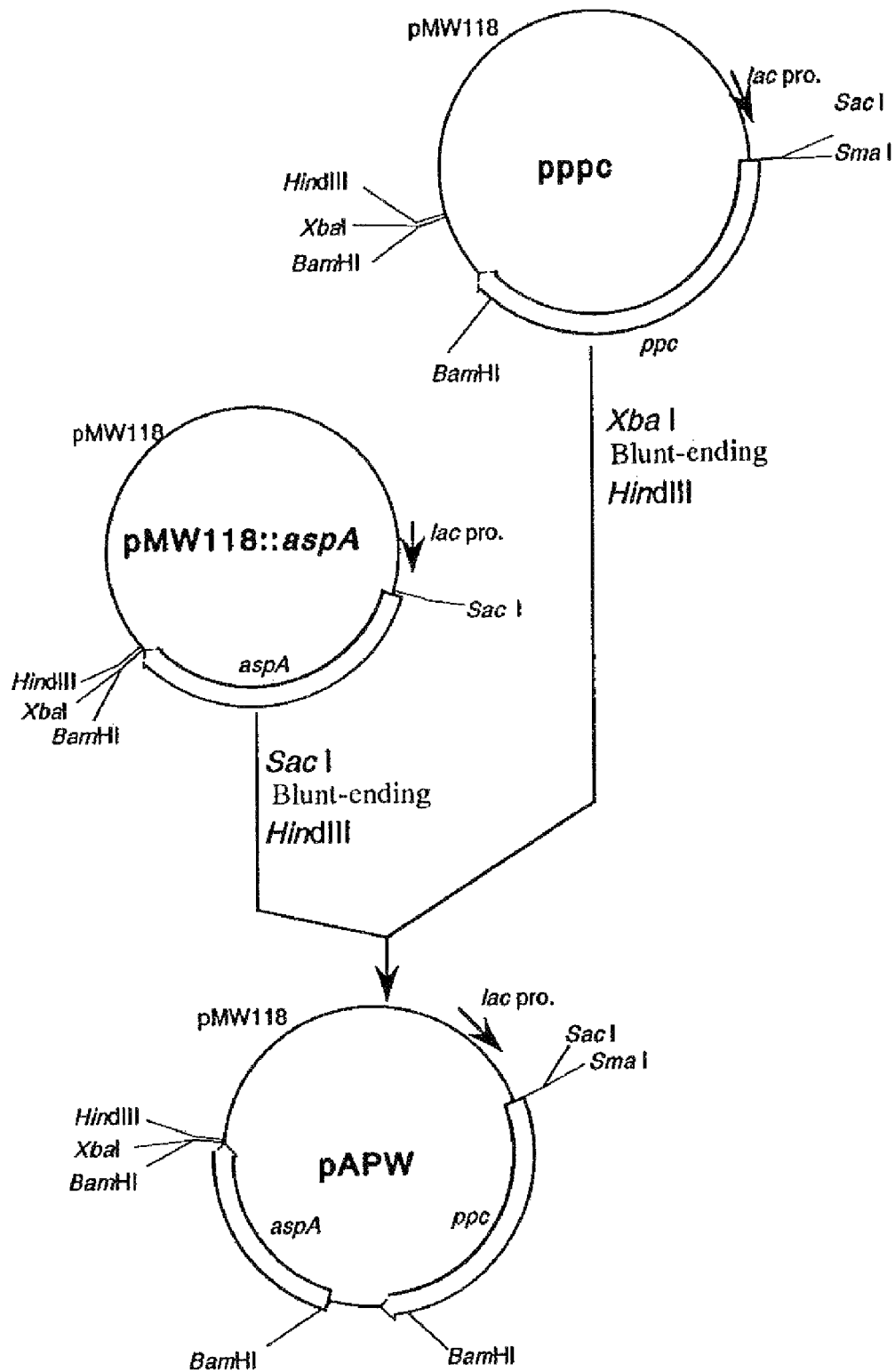
FIG. 12 shows a process of producing the plasmid pAPW containing ppc and aspA.

The plasmid pMW118::aspA described in the aforementioned Example 1 was digested with SacI, blunt-ended at both ends, and further digested with HindIII to obtain a DNA fragment containing aspA. Then, pppc (see International Publication No. WO95/16042) was digested with XbaI, blunt-ended for the both ends, and further digested with HindIII, and the previously obtained aspA fragment was inserted into the HindIII cleavage site to obtain pAPW (FIG. 12).

<2> Introduction of Two Kinds of Genes and Evaluation of L-Lysine Productivity

To a pCABD2-introduced transformant which was obtained in the aforementioned Example 1, each of pppc (reference plasmid), ppcd, pPTS and pAPW (comparative plasmid) was introduced. The obtained transformants contained two kinds of plasmids, i.e. one of pppc, ppcd, pPTS and pAPW, and pCABD2. These transformants were examined for the L-lysine productivity in the same manner as in Example 1 <2>.

The results are shown in Table 2.

TABLE 2

| | Lys accumulation (mg/dl) |
|---|---|
| pCABD2 + pppc | 1380 |
| pCABD2 + ppcd | 1460 |
| pCABD2 + pPTS | 1450 |
| pCABD2 + pAPW | 1390 |

As clearly seen from the results shown in Table 2, when asd or pntAB was enhanced together with dapA+lysC+dapB+ ddh+ppc (ppcd or pPTS), marked increase of the L-lysine production amount was observed (80 mg/dl as for asd, 70 mg/dl as for pntAB). As for aspA, however, even when aspA was enhanced together with dapA+lysC+dapB+ddh+ppc (pAPW), marked increase of the L-lysine production amount was not observed.

Example 3

<1> Construction of Plasmids Containing Phosphoenolpyruvate Carboxylase Gene (ppc), Transhydrogenase Gene (pntAB) and Aspartate-Semialdehyde Dehydrogenase Gene (asd) or Aspartase Gene (aspA)

A plasmid containing ppc, pntAB and asd genes and a plasmid containing ppc, pntAB and aspA were constructed as follows.

(1) Plasmid Containing ppc, pntAB and asd (pPTd)

Figure 13:
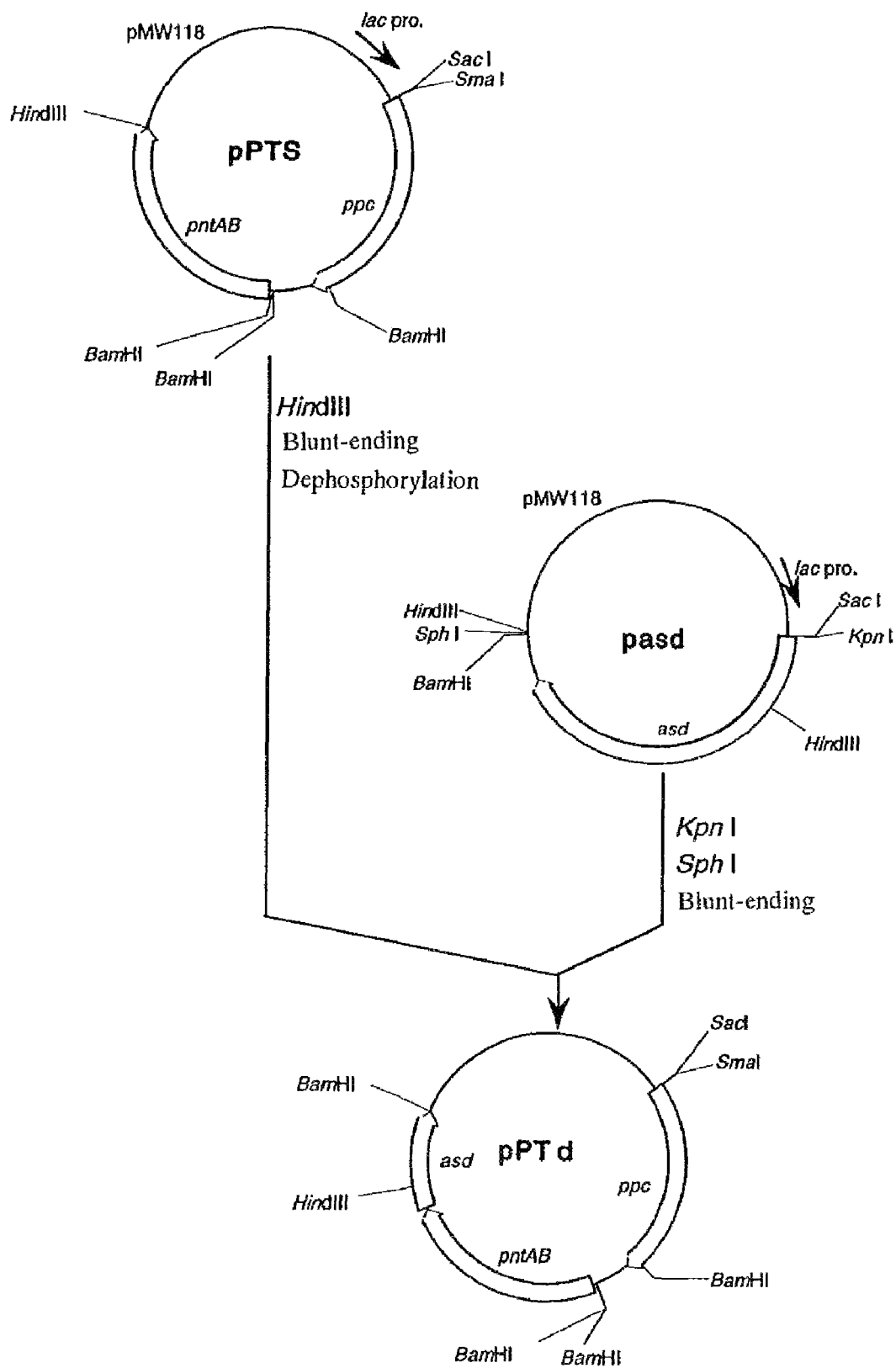
FIG. 13 shows a process of producing the plasmid pPTd containing ppc, pntAB, and asd.

The plasmid pasd (see International Publication No. WO95/16042) was digested with KpnI and SphI, and the DNA fragment containing asd was blunt-ended for the both ends. Then, pPTS described in the aforementioned Example 2 was digested with HindIII and blunt-ended, and the previously obtained asd fragment was inserted into the HindIII cleavage site to obtain pPTd (FIG. 13).

(2) Plasmid Containing ppc, pntAB and aspA (pAPT)

Figure 14:
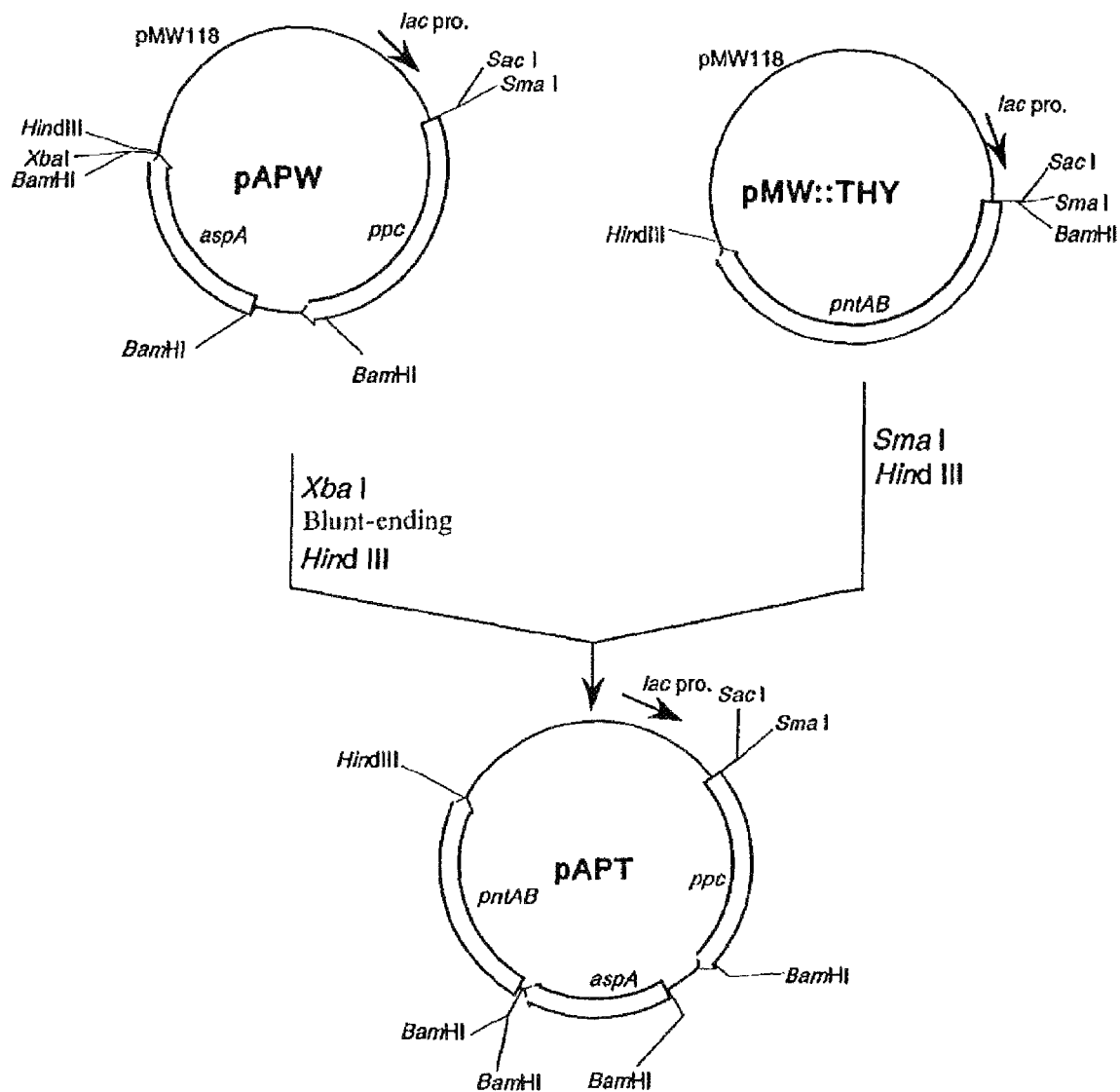
FIG. 14 shows a process of producing the plasmid pAPT containing ppc, pntAB, and aspA.

The plasmid pMW::THY (see International Publication No. WO95/11985) was digested with SmaI and HindIII to obtain a DNA fragment containing pntAB. Then, pAPW described in the aforementioned Example 2 was digested with XbaI, blunt-ended for the both ends, and further digested with HindIII. The previously obtained fragment containing pntAB was inserted into the HindIII cleavage site to obtain pAPT (FIG. 14).

<2> Introduction of Three Kinds of Genes and Evaluation of L-Lysine Productivity To a pCABD2-introduced transformant which was obtained in the aforementioned Example 1, pPTS (reference plasmid), pPTd or pAPT was introduced. The obtained transformants contained two kinds of plasmids, i.e. one of pPTS, pPTd and pAPT, and pCABD2. These transformants were examined for the L-lysine productivity in the same manner as in Example 1 <2>.

The results are shown in Table 3.

TABLE 3

| | Lys accumulation (mg/dl) |
|---|---|
| pCABD2 + pPTS | 1450 |
| pCABD2 + pPTd | 1510 |
| pCABD2 + pAPT | 1500 |

As clearly seen from the results shown in Table 3, when asd or aspA was enhanced together with dapA+lysC+dapB+ddh+ppc+pntAB (pPTd or pAPT), marked increase of the L-lysine production amount was observed (60 mg/dl as for asd, 50 mg/dl as for aspA).

Example 4

<1> Construction of Plasmids Containing Phosphoenolpyruvate Carboxylase Gene (ppc), Transhydrogenase Gene (pntAB), Aspartate-Semialdehyde Dehydrogenase Gene (asd) and Aspartase (aspA) Gene A plasmid containing ppc, pntAB, asd and aspA was constructed as follows.

Figure 15:
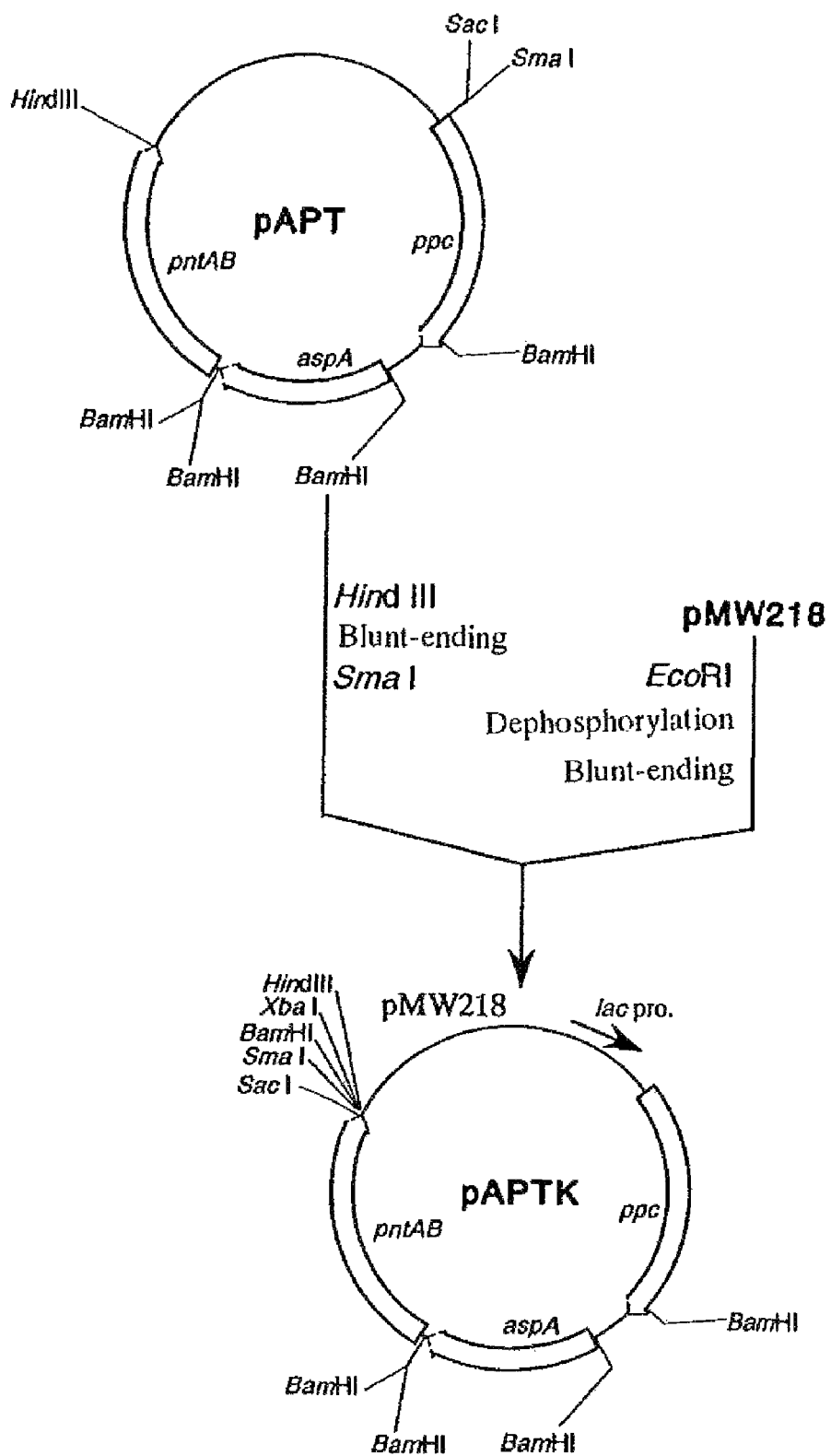
FIG. 15 shows a process of producing the plasmid pAPTK containing ppc, pntAB, and aspA.

The plasmid pAPT described in the aforementioned Example 3 was digested with HindIII, blunt-ended for the both ends, and further digested with SmaI to obtain a DNA fragment containing ppc, aspA and pntAB. Then, pMW218 (Nippon Gene) was digested with EcoRI and blunt-ended for the both ends, and the previously obtained DNA fragment containing ppc, aspA and pntAB was inserted into the blunt-ended EcoRI cleavage site to obtain pAPTK (FIG. 15).

Figure 16:
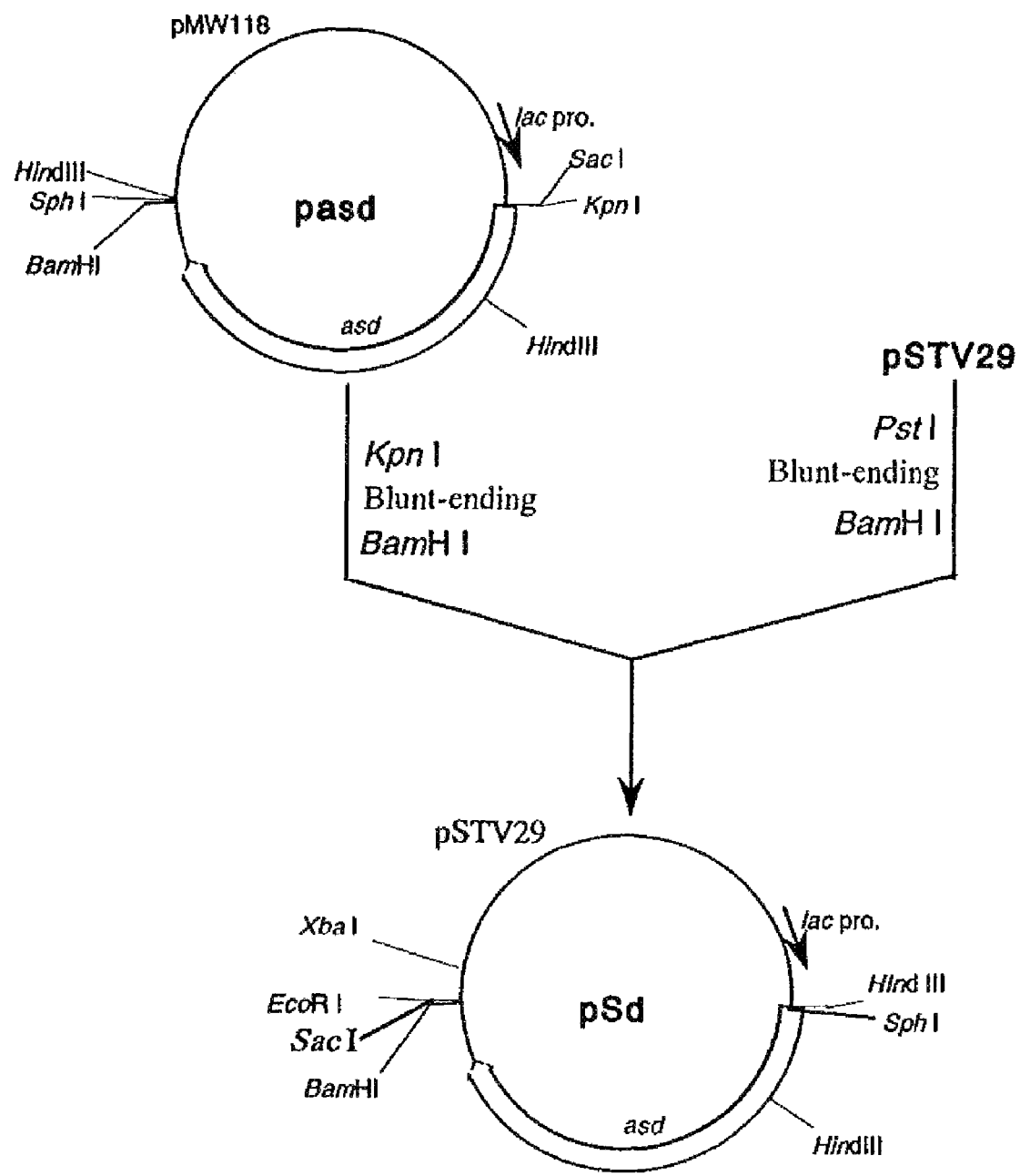
FIG. 16 shows a process of producing the plasmid pSd containing asd.

Then, pasd described in International Publication No. WO95/16042 was digested with KpnI, blunt-ended for the both ends, and further digested with BamHI to obtain a DNA fragment containing asd. Then, pSTV29 was digested with PstI, blunt-ended for the both ends, and inserted with the previously obtained asd fragment at the BamHI cleavage site to obtain pSd (FIG. 16).

Figure 17:
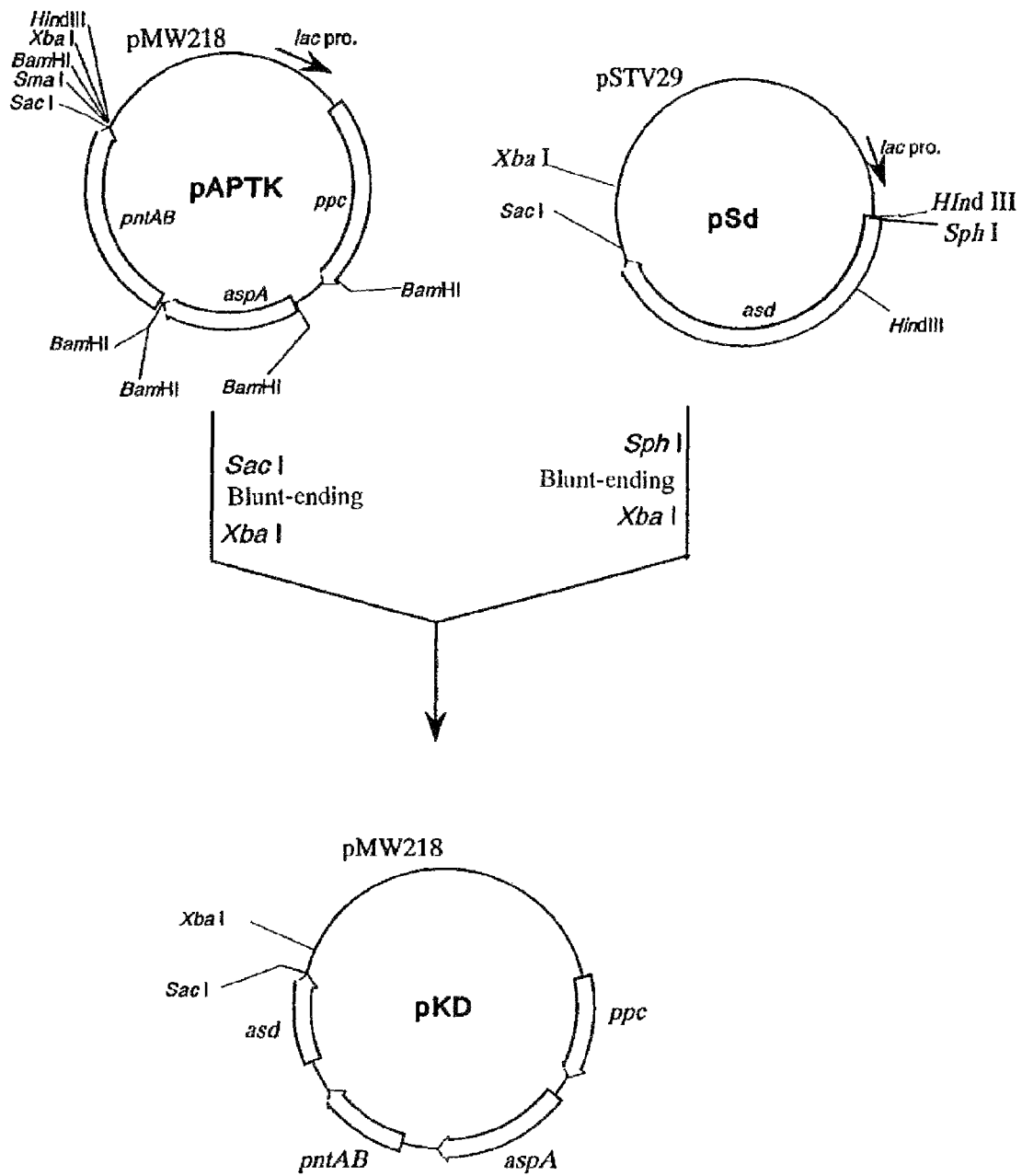
FIG. 17 shows a process of producing the plasmid pKD containing ppc, pntAB, aspA, and asd.

Then, pSd was digested with SphI, blunt-ended for the both ends, and further digested with XbaI to obtain a DNA fragment containing asd again. Then, pAPTK was digested with SadI and blunt-ended for the both ends, and the previously obtained asd fragment was inserted at the XbaI cleavage site to obtain pKD (FIG. 17).

<2> Introduction of Four Kinds of Genes and Evaluation of L-Lysine Productivity

To a transformant into which pCABD2, pCABD(B) or pCABDE1 was introduced, which were obtained in the aforementioned Example 1, pAPT (Reference plasmid 1), pAPTK (Reference plasmid 2) or pKD was introduced. The obtained transformants contained two kinds of plasmids, i.e. one of pAPT, pAPTK and pKD, and one of pCABD2, pCABD(B) and pCABDE1. These transformants were examined for the L-lysine productivity in the same manner as in Example 1 <2>.

The results are shown in Table 4.

TABLE 4

| | Lys accumulation (mg/dl) |
|---|---|
| pCABD2 + pAPT | 1500 |
| pCABD2 + pAPTK | 1500 |
| pCABD2 + pKD | 1600 |
| pCABD(B) + pKD | 1590 |
| pCABDE1 + pKD | 1580 |

As clearly seen from the results shown in Table 4, when asd was enhanced together with dapA+lysC+dapB+ddh+ppc+pntAB+aspA, marked increase of the L-lysine production amount was observed. A similar result was obtained when pCABD(B) or pCABDE1 was used instead of pCABD2.

The plasmid pAPTK mentioned in Table 4 corresponded to pAPT of which drug resistance gene was changed from that for ampicillin to that for kanamycin (because the vector was changed from pMW118 to pMW218). Since pKD was prepared by inserting asd into pAPTK, it was considered that pAPTK was more suitable than pAPT as control of pKD. Therefore, the data of pAPTK is also shown. It was also confirmed that the L-lysine production amount was not influenced even if the drug resistance gene was changed.

INDUSTRIAL APPLICABILITY

The present invention provides *Escherichia* bacteria with high L-lysine productivity, and L-lysine can be obtained with a high yield by using these bacteria.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method of producing L-lysine comprising:
   A) culturing in a medium an *Escherichia coli* bacterium in which:
   (a) the intracellular activities of all of the following enzymes are enhanced:
      dihydrodipicolinate synthase which comprises a mutation replacing at least one amino acid selected from the group consisting of the alanine at the 81st position and the histidine at the 118th position with another amino acid, wherein the amino acid sequence of said dihydrodipicolinate synthase prior to said mutation(s) is the amino acid sequence of wild-type dihydrodipicolinate synthase of *Escherichia coli*, aspartokinase, dihydrodipicolinate reductase, phosphoenolpyruvate carboxylase, nicotinamide adenine dinucleotide transhydrogenase, and aspartate-semialdehyde dehydrogenase; and (b) the intracellular activities of at least one of the following enzymes are enhanced: i) diaminopimelate dehydrogenase, or
ii) tetrahydrodipicolinate succinylase and succinyldiaminopimelate deacylase, wherein said activities are enhanced by a method selected from the group consisting of
a) introducing a promoter or promoters which are operably linked to the gene encoding the enzymes into the chromosome of said bacterium,
b) increasing the copy number of the genes encoding the enzymes by introducing one or more expression vectors into said bacterium, and
c) combinations thereof;
B) allowing L-lysine to accumulate in said medium or said bacterium; and
C) collecting L-lysine from the medium or the bacterium.

2. The method according to claim 1, wherein said aspartokinase comprises a mutation selected from the group consisting of:
(a) replacement of the glycine at the 323rd position with another amino acid;
(b) replacement of the glycine at the 323rd and 408th positions with another amino acid;
(c) replacement of the arginine at the 34th position and the glycine at the 323rd position with another amino acid;
(d) replacement of the leucine at the 325th position with another amino acid;
(e) replacement of the methionine at the 318th position with another amino acid;
(f) replacement of the methionine at the 318th position and the valine at the 349th position with another amino acid;
(g) replacement of the serine at the 345th position with another amino acid;
(h) replacement of the valine at the 347th position with another amino acid;
(i) replacement of the threonine at the 352nd position with another amino acid;
(j) replacement of the threonine at the 352nd position and serine at the 369th position with another amino acid;
(k) replacement of the glutamic acid at the 164th position with another amino acid;
(l) replacement of the methionine at the 417th position and the cysteine at the 419th position with another amino acid;
(m) replacement of the glycine at the 323rd position and the methionine at the 318th position with another amino acid; and
(n) combinations thereof,
wherein the amino acid sequence of said aspartokinase prior to said mutation(s) is the amino acid sequence of wild-type aspartokinase III of *Escherichia coli*.

3. The method of claim 1, wherein the alanine at the $81^{st}$ position is replaced with valine, and the histidine at the $118^{th}$ position is replaced with tyrosine.

4. The method of claim 2, wherein
(a) the glycine at the $323^{rd}$ position is replaced with aspartic acid;
(b) the glycine at the $323^{rd}$ and $408^{th}$ positions is replaced with aspartic acid;
(c) the arginine at the $34^{th}$ position is replaced with cysteine and the glycine at the $323^{rd}$ position is replaced with aspartic acid;
(d) the leucine at the $325^{th}$ position is replaced with phenylalanine;
(e) the methionine at the $318^{th}$ position is replaced with isoleucine;
(f) the methionine at the $318^{th}$ position is replaced with isoleucine and the valine at the $349^{th}$ position is replaced with methionine;
(g) the serine at the $345^{th}$ position is replaced with leucine;
(h) the valine at the $347^{th}$ position is replaced with methionine;
(i) the threonine at the $352^{nd}$ position is replaced with isoleucine;
(j) the threonine at the $352^{nd}$ position is replaced with isoleucine and the serine at the $369^{th}$ position is replaced with phenylalanine;
(k) the glutamic acid at the $164^{th}$ position is replaced with lysine;
(l) the methionine at the $417^{th}$ position is replaced with isoleucine and the cysteine at the $419^{th}$ position is replaced with tyrosine;
(m) the glycine at the $323^{rd}$ position is replaced with aspartic acid and the methionine at the $318^{th}$ position is replaced with isoleucine.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer for amplification of a promoter portion
      of tet

<400> SEQUENCE: 1
tcaagaattc tcatgtttga                                               20
```

```
<210> SEQ ID NO 2
<211> LENGTH: 35
<212> TYPE: DNA
<213> ORGANISM: Artificial Sequence
<220> FEATURE:
<223> OTHER INFORMATION: Primer for amplification of a promoter portion
      of tet

<400> SEQUENCE: 2
gttagatttg gtacccggtg cctgactgcg ttagc                              35

<210> SEQ ID NO 3
<211> LENGTH: 30
<212> TYPE: DNA
<213> ORGANISM: Artificial Sequence
<220> FEATURE:
<223> OTHER INFORMATION: Primer for amplification of dapA

<400> SEQUENCE: 3
ggttgtggta cccccaaatg agggaagaag                                    30

<210> SEQ ID NO 4
<211> LENGTH: 20
<212> TYPE: DNA
<213> ORGANISM: Artificial Sequence
<220> FEATURE:
<223> OTHER INFORMATION: Primer for amplification of dapA

<400> SEQUENCE: 4
tggaacctct gttgctgcag                                               20

<210> SEQ ID NO 5
<211> LENGTH: 20
<212> TYPE: DNA
<213> ORGANISM: Artificial Sequence
<220> FEATURE:
<223> OTHER INFORMATION: Primer for amplification of aspA

<400> SEQUENCE: 5
tgatcagcga aacactttta                                               20

<210> SEQ ID NO 6
<211> LENGTH: 19
<212> TYPE: DNA
<213> ORGANISM: Artificial Sequence
<220> FEATURE:
<223> OTHER INFORMATION: Primer for amplification of aspA

<400> SEQUENCE: 6
cagcaaacta tgatgagaa                                                19
```